US007354744B2

(12) United States Patent
Takahashi et al.

(10) Patent No.: US 7,354,744 B2
(45) Date of Patent: Apr. 8, 2008

(54) PROCESS FOR PRODUCING L-GLUTAMIC ACID

(75) Inventors: Yusuke Takahashi, Kawasaki (JP); Yasuhiro Tateyama, Kawasaki (JP); Masakazu Sato, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 283 days.

(21) Appl. No.: 11/297,383

(22) Filed: Dec. 9, 2005

(65) Prior Publication Data

US 2006/0110813 A1 May 25, 2006

Related U.S. Application Data

(63) Continuation of application No. PCT/JP2004/008140, filed on Jun. 10, 2004.

(30) Foreign Application Priority Data

Jun. 10, 2003 (JP) ............................ 2003-165545

(51) Int. Cl.
*C12P 13/04* (2006.01)

(52) U.S. Cl. ...................................................... 435/110

(58) Field of Classification Search ................. 435/110
See application file for complete search history.

(56) References Cited

U.S. PATENT DOCUMENTS 6,197,559 B1 3/2001 Moriya et al.
6,331,419 B1 12/2001 Moriya et al.
6,596,517 B2 7/2003 Izui et al.
6,653,110 B2 11/2003 Sato et al.

FOREIGN PATENT DOCUMENTS

| | | |
|---|---|---|
| EP | 0 999 282 | 5/2000 |
| EP | 1 078 989 | 2/2001 |
| EP | 1 382 686 | 1/2004 |
| EP | 1 352 966 | 7/2005 |
| EP | 1 233 069 | 9/2005 |
| JP | 61-139398 | 6/1986 |

OTHER PUBLICATIONS

International Search Report for PCT Appl. No. PCT/JP2004/008140, dated Jul. 20, 2004.

International Preliminary Report on Patentability for PCT App. No. PCT/JP2004/0084140 (May 11, 2006).

*Primary Examiner*—Herbert J. Lilling
(74) *Attorney, Agent, or Firm*—Shelly Guest Cermak Cermak Kenealy & Vaidya LLP

(57) ABSTRACT

L-glutamic acid is produced by culturing in a liquid medium containing L-glutamic acid at a saturation concentration and the carbon source a microorganism that can metabolize a carbon source at a specific pH, and wherein said microorganism has an ability to accumulate L-glutamic acid in said medium in an amount which exceeds the the saturation concentration of L-glutamic acid, wherein the pH of said medium is controlled so that L-glutamic acid precipitates.

4 Claims, 7 Drawing Sheets

SEQUENCE LISTING

```
<160> NUMBER OF SEQ ID NOS: 13

<210> SEQ ID NO 1
<211> LENGTH: 4556
<212> TYPE: DNA
<213> ORGANISM: Pantoea ananatis
<220> FEATURE:
<221> NAME/KEY: CDS
<222> LOCATION: (2)..(121)
<220> FEATURE:
<221> NAME/KEY: CDS
<222> LOCATION: (322)..(3129)
<220> FEATURE:
<221> NAME/KEY: CDS
<222> LOCATION: (3145)..(4368)
<220> FEATURE:
<221> NAME/KEY: CDS
<222> LOCATION: (4437)..(4556)

<400> SEQUENCE: 1

t gca ttc agc gtt ttc cgc tgt cac agc atc atg aac tgt gta agt gtt      49
  Ala Phe Ser Val Phe Arg Cys His Ser Ile Met Asn Cys Val Ser Val
    1               5                  10                  15

tgt cct aaa ggg cta aac ccg acg cgc gct atc ggc cac att aag tcg       97
Cys Pro Lys Gly Leu Asn Pro Thr Arg Ala Ile Gly His Ile Lys Ser
             20                  25                  30

atg ctg ctg caa cgc agc gcg tagttatacc accgggaacc tcaggttccc        148
Met Leu Leu Gln Arg Ser Ala
```

-continued

```
        35

ggtattttac ggaagcctct gtaaacgcgg tcccaaccac gtttacaaag gttcccttac    208

gggccgggcg cgcgctgcgc acagtgctcg tatcgctgaa ctcactacgg caaaccgcga    268

aagcggcaac aaatgaaacc tcaaaaaagc ataacattgc ttaagggatc aca atg       324
                                                            Met
                                                              1

cag aac agc gcg atg aag ccc tgg ctg gac tcc tcc tgg ctg gcc ggc      372
Gln Asn Ser Ala Met Lys Pro Trp Leu Asp Ser Ser Trp Leu Ala Gly
              5                  10                  15

gcg aat cag tct tac ata gag caa ctc tat gag gat ttc ctg acc gat      420
Ala Asn Gln Ser Tyr Ile Glu Gln Leu Tyr Glu Asp Phe Leu Thr Asp
         20                  25                  30

cct gac tct gtg gat gca gtg tgg cgc tcg atg ttc caa cag tta cca      468
Pro Asp Ser Val Asp Ala Val Trp Arg Ser Met Phe Gln Gln Leu Pro
     35                  40                  45

ggc acg gga gtg aaa cct gag cag ttc cac tcc gca act cgc gaa tat      516
Gly Thr Gly Val Lys Pro Glu Gln Phe His Ser Ala Thr Arg Glu Tyr
 50                  55                  60                  65

ttc cgt cgc ctg gcg aaa gac gca tct cgt tac acc tcc tca gtt acc      564
Phe Arg Arg Leu Ala Lys Asp Ala Ser Arg Tyr Thr Ser Ser Val Thr
                 70                  75                  80

gat ccg gca acc aac tcc aaa caa gtg aaa gtg ctg cag ctg att aac      612
Asp Pro Ala Thr Asn Ser Lys Gln Val Lys Val Leu Gln Leu Ile Asn
             85                  90                  95

gcg ttt cgt ttc cgc gga cat cag gaa gca aat ctc gat ccg ctt ggc      660
Ala Phe Arg Phe Arg Gly His Gln Glu Ala Asn Leu Asp Pro Leu Gly
        100                 105                 110

ctg tgg aaa cag gac cgc gtt gcc gat ctc gat cct gcc ttt cac gat      708
Leu Trp Lys Gln Asp Arg Val Ala Asp Leu Asp Pro Ala Phe His Asp
    115                 120                 125

ctg acc gac gcc gat ttt cag gaa agc ttt aac gta ggt tct ttt gcc      756
Leu Thr Asp Ala Asp Phe Gln Glu Ser Phe Asn Val Gly Ser Phe Ala
130                 135                 140                 145

att ggc aaa gaa acc atg aag ctg gcc gat ctg ttc gac gcg ctg aag      804
Ile Gly Lys Glu Thr Met Lys Leu Ala Asp Leu Phe Asp Ala Leu Lys
                150                 155                 160

cag acc tac tgt ggc tcg att ggt gca gag tat atg cac atc aat aac      852
Gln Thr Tyr Cys Gly Ser Ile Gly Ala Glu Tyr Met His Ile Asn Asn
            165                 170                 175

acc gaa gag aaa cgc tgg atc cag cag cgt atc gaa tcc ggt gcg agc      900
Thr Glu Glu Lys Arg Trp Ile Gln Gln Arg Ile Glu Ser Gly Ala Ser
        180                 185                 190

cag acg tca ttc agt ggc gaa gag aaa aaa ggt ttc ctg aaa gag ctg      948
Gln Thr Ser Phe Ser Gly Glu Glu Lys Lys Gly Phe Leu Lys Glu Leu
    195                 200                 205

acc gcg gca gaa ggg ctg gaa aaa tat ctg ggc gcg aaa ttc ccg ggt      996
Thr Ala Ala Glu Gly Leu Glu Lys Tyr Leu Gly Ala Lys Phe Pro Gly
210                 215                 220                 225

gca aaa cgt ttc tcg ctg gaa ggc ggt gat gcg ctg gtg ccg atg ctg     1044
Ala Lys Arg Phe Ser Leu Glu Gly Gly Asp Ala Leu Val Pro Met Leu
                230                 235                 240

cgc gag atg att cgt cat gcg ggc aaa agc ggc aca cgt gaa gtg gta     1092
Arg Glu Met Ile Arg His Ala Gly Lys Ser Gly Thr Arg Glu Val Val
            245                 250                 255

ctg ggg atg gcg cac cgt ggc cgt ctt aac gta ctg att aac gta ctg     1140
Leu Gly Met Ala His Arg Gly Arg Leu Asn Val Leu Ile Asn Val Leu
        260                 265                 270

ggt aaa aag cca cag gat ctg ttc gac gaa ttc tcc ggt aaa cac aaa     1188
```

-continued

```
Gly Lys Lys Pro Gln Asp Leu Phe Asp Glu Phe Ser Gly Lys His Lys
    275                 280                 285

gag cat ctg ggc acc ggt gat gtg aag tat cac atg ggc ttc tct tcg      1236
Glu His Leu Gly Thr Gly Asp Val Lys Tyr His Met Gly Phe Ser Ser
290                 295                 300                 305

gat att gaa acc gaa ggt ggt ctg gtg cat ctg gcg ctg gcg ttt aac      1284
Asp Ile Glu Thr Glu Gly Gly Leu Val His Leu Ala Leu Ala Phe Asn
                310                 315                 320

ccg tct cac ctg gaa att gtc agc ccg gtg gtc atg gga tcg gta cgt      1332
Pro Ser His Leu Glu Ile Val Ser Pro Val Val Met Gly Ser Val Arg
            325                 330                 335

gca cgt ctc gat cgt ctg gcc gaa ccg gtc agc aat aaa gtg ttg cct      1380
Ala Arg Leu Asp Arg Leu Ala Glu Pro Val Ser Asn Lys Val Leu Pro
        340                 345                 350

atc acc att cac ggt gat gcg gcg gtg att ggt cag ggc gtg gtt cag      1428
Ile Thr Ile His Gly Asp Ala Ala Val Ile Gly Gln Gly Val Val Gln
    355                 360                 365

gaa acc ctg aac atg tct cag gcg cgc ggc tac gaa gtg ggc ggc acg      1476
Glu Thr Leu Asn Met Ser Gln Ala Arg Gly Tyr Glu Val Gly Gly Thr
370                 375                 380                 385

gta cgt atc gtc att aac aac cag gtt ggt ttt acc acc tcc aac ccg      1524
Val Arg Ile Val Ile Asn Asn Gln Val Gly Phe Thr Thr Ser Asn Pro
                390                 395                 400

aaa gat gcg cgt tca acc ccg tac tgt act gac atc ggc aag atg gtg      1572
Lys Asp Ala Arg Ser Thr Pro Tyr Cys Thr Asp Ile Gly Lys Met Val
            405                 410                 415

ctg gca ccg att ttc cac gtc aat gct gac gat ccg gaa gcg gtg gcc      1620
Leu Ala Pro Ile Phe His Val Asn Ala Asp Asp Pro Glu Ala Val Ala
        420                 425                 430

ttt gtt acc cgc ctg gcg ctg gac tat cgc aac acc ttc aaa cgc gat      1668
Phe Val Thr Arg Leu Ala Leu Asp Tyr Arg Asn Thr Phe Lys Arg Asp
    435                 440                 445

gtg ttt atc gat ctg gtg tgc tat cgc cgt cat ggt cac aac gag gcg      1716
Val Phe Ile Asp Leu Val Cys Tyr Arg Arg His Gly His Asn Glu Ala
450                 455                 460                 465

gat gag cca agt gct acc cag ccg ttg atg tac cag aaa atc aaa aag      1764
Asp Glu Pro Ser Ala Thr Gln Pro Leu Met Tyr Gln Lys Ile Lys Lys
                470                 475                 480

cat ccg acg ccg cgt aaa att tac gcc gat cgt ctg gaa ggc gaa ggt      1812
His Pro Thr Pro Arg Lys Ile Tyr Ala Asp Arg Leu Glu Gly Glu Gly
            485                 490                 495

gtc gcg tcg cag gaa gat gcc acc gag atg gtg aac ctg tac cgc gat      1860
Val Ala Ser Gln Glu Asp Ala Thr Glu Met Val Asn Leu Tyr Arg Asp
        500                 505                 510

gcg ctc gat gcg ggc gaa tgc gtg gtg ccg gaa tgg cgt ccg atg agc      1908
Ala Leu Asp Ala Gly Glu Cys Val Val Pro Glu Trp Arg Pro Met Ser
    515                 520                 525

ctg cac tcc ttc acg tgg tcg cct tat ctg aac cac gaa tgg gat gag      1956
Leu His Ser Phe Thr Trp Ser Pro Tyr Leu Asn His Glu Trp Asp Glu
530                 535                 540                 545

cct tat ccg gca cag gtt gac atg aaa cgc ctg aag gaa ctg gca ttg      2004
Pro Tyr Pro Ala Gln Val Asp Met Lys Arg Leu Lys Glu Leu Ala Leu
                550                 555                 560

cgt atc agc cag gtc cct gag cag att gaa gtg cag tcg cgc gtg gcc      2052
Arg Ile Ser Gln Val Pro Glu Gln Ile Glu Val Gln Ser Arg Val Ala
            565                 570                 575

aag atc tat aac gat cgc aag ctg atg gcc gaa ggc gag aaa gcg ttc      2100
Lys Ile Tyr Asn Asp Arg Lys Leu Met Ala Glu Gly Glu Lys Ala Phe
        580                 585                 590
```

-continued

```
gac tgg ggc ggt gcc gag aat ctg gcg tac gcc acg ctg gtg gat gaa     2148
Asp Trp Gly Gly Ala Glu Asn Leu Ala Tyr Ala Thr Leu Val Asp Glu
    595                 600                 605

ggt att ccg gtt cgc ctc tcg ggt gaa gac tcc ggt cgt gga acc ttc     2196
Gly Ile Pro Val Arg Leu Ser Gly Glu Asp Ser Gly Arg Gly Thr Phe
610                 615                 620                 625

ttc cat cgc cac gcg gtc gtg cac aac cag gct aac ggt tca acc tat     2244
Phe His Arg His Ala Val Val His Asn Gln Ala Asn Gly Ser Thr Tyr
                630                 635                 640

acg ccg ctg cac cat att cat aac agc cag ggc gag ttc aaa gtc tgg     2292
Thr Pro Leu His His Ile His Asn Ser Gln Gly Glu Phe Lys Val Trp
            645                 650                 655

gat tcg gtg ctg tct gaa gaa gcg gtg ctg gcg ttt gaa tac ggt tac     2340
Asp Ser Val Leu Ser Glu Glu Ala Val Leu Ala Phe Glu Tyr Gly Tyr
        660                 665                 670

gcc acg gct gag ccg cgc gtg ctg acc atc tgg gaa gcg cag ttt ggt     2388
Ala Thr Ala Glu Pro Arg Val Leu Thr Ile Trp Glu Ala Gln Phe Gly
    675                 680                 685

gac ttt gcc aac ggt gct cag gtg gtg att gac cag ttc atc agc tct     2436
Asp Phe Ala Asn Gly Ala Gln Val Val Ile Asp Gln Phe Ile Ser Ser
690                 695                 700                 705

ggc gaa cag aag tgg ggc cgt atg tgt ggc ctg gtg atg ttg ctg ccg     2484
Gly Glu Gln Lys Trp Gly Arg Met Cys Gly Leu Val Met Leu Leu Pro
                710                 715                 720

cat ggc tac gaa ggt cag gga ccg gaa cac tcc tct gcc cgt ctg gaa     2532
His Gly Tyr Glu Gly Gln Gly Pro Glu His Ser Ser Ala Arg Leu Glu
            725                 730                 735

cgc tat ctg caa ctt tgc gcc gag cag aac atg cag gtt tgc gtc ccg     2580
Arg Tyr Leu Gln Leu Cys Ala Glu Gln Asn Met Gln Val Cys Val Pro
        740                 745                 750

tcg acg ccg gct cag gtg tat cac atg ctg cgc cgt cag gcg ctg cgc     2628
Ser Thr Pro Ala Gln Val Tyr His Met Leu Arg Arg Gln Ala Leu Arg
    755                 760                 765

ggg atg cgc cgt ccg ctg gtg gtg atg tcg ccg aag tcg ctg tta cgc     2676
Gly Met Arg Arg Pro Leu Val Val Met Ser Pro Lys Ser Leu Leu Arg
770                 775                 780                 785

cat cca ctg gcg atc tcg tcg ctg gat gaa ctg gca aac ggc agt ttc     2724
His Pro Leu Ala Ile Ser Ser Leu Asp Glu Leu Ala Asn Gly Ser Phe
                790                 795                 800

cag ccg gcc att ggt gag atc gac gat ctg gat ccg cag ggc gtg aaa     2772
Gln Pro Ala Ile Gly Glu Ile Asp Asp Leu Asp Pro Gln Gly Val Lys
            805                 810                 815

cgc gtc gtg ctg tgc tcc ggt aag gtt tac tac gat ctg ctg gaa cag     2820
Arg Val Val Leu Cys Ser Gly Lys Val Tyr Tyr Asp Leu Leu Glu Gln
        820                 825                 830

cgt cgt aaa gac gag aaa acc gat gtt gcc atc gtg cgc atc gaa cag     2868
Arg Arg Lys Asp Glu Lys Thr Asp Val Ala Ile Val Arg Ile Glu Gln
    835                 840                 845

ctt tac ccg ttc ccg cat cag gcg gta cag gaa gca ttg aaa gcc tat     2916
Leu Tyr Pro Phe Pro His Gln Ala Val Gln Glu Ala Leu Lys Ala Tyr
850                 855                 860                 865

tct cac gta cag gac ttt gtc tgg tgc cag gaa gag cct ctg aac cag     2964
Ser His Val Gln Asp Phe Val Trp Cys Gln Glu Glu Pro Leu Asn Gln
                870                 875                 880

ggc gcc tgg tac tgt agc cag cat cat ttc cgt gat gtc gtg ccg ttt     3012
Gly Ala Trp Tyr Cys Ser Gln His His Phe Arg Asp Val Val Pro Phe
            885                 890                 895

ggt gcc acc ctg cgt tat gca ggt cgc ccg gca tcg gct tct ccg gcc     3060
Gly Ala Thr Leu Arg Tyr Ala Gly Arg Pro Ala Ser Ala Ser Pro Ala
        900                 905                 910
```

-continued

```
gtg ggt tat atg tcc gta cac caa caa cag cag caa gac ctg gtt aat     3108
Val Gly Tyr Met Ser Val His Gln Gln Gln Gln Gln Asp Leu Val Asn
    915                 920                 925

gac gca ctg aac gtc aat taattaaaag gaaagata atg agt agc gta gat     3159
Asp Ala Leu Asn Val Asn                     Met Ser Ser Val Asp
930                 935                           1               5

att ctc gtt ccc gac ctg cct gaa tcg gtt gca gat gcc aca gta gca     3207
Ile Leu Val Pro Asp Leu Pro Glu Ser Val Ala Asp Ala Thr Val Ala
                 10                  15                  20

acc tgg cac aag aaa cca ggc gat gca gtc agc cgc gat gaa gtc atc     3255
Thr Trp His Lys Lys Pro Gly Asp Ala Val Ser Arg Asp Glu Val Ile
             25                  30                  35

gtc gaa att gaa act gac aaa gtc gtg ctg gaa gtg ccg gca tct gcc     3303
Val Glu Ile Glu Thr Asp Lys Val Val Leu Glu Val Pro Ala Ser Ala
         40                  45                  50

gat ggc gtg ctg gaa gcc gtg ctg gaa gac gaa ggg gca acc gtt acg     3351
Asp Gly Val Leu Glu Ala Val Leu Glu Asp Glu Gly Ala Thr Val Thr
     55                  60                  65

tcc cgc cag atc ctg ggt cgc ctg aaa gaa ggc aac agt gcg ggt aaa     3399
Ser Arg Gln Ile Leu Gly Arg Leu Lys Glu Gly Asn Ser Ala Gly Lys
 70                  75                  80                  85

gaa agc agt gcc aaa gcg gaa agc aat gac acc acg cca gcc cag cgt     3447
Glu Ser Ser Ala Lys Ala Glu Ser Asn Asp Thr Thr Pro Ala Gln Arg
                 90                  95                 100

cag aca gcg tcg ctt gaa gaa gag agc agc gat gcg ctc agc ccg gcg     3495
Gln Thr Ala Ser Leu Glu Glu Glu Ser Ser Asp Ala Leu Ser Pro Ala
            105                 110                 115

atc cgt cgc ctg att gcg gag cat aat ctt gac gct gcg cag atc aaa     3543
Ile Arg Arg Leu Ile Ala Glu His Asn Leu Asp Ala Ala Gln Ile Lys
        120                 125                 130

ggc acc ggc gta ggc gga cgt tta acg cgt gaa gac gtt gaa aaa cat     3591
Gly Thr Gly Val Gly Gly Arg Leu Thr Arg Glu Asp Val Glu Lys His
    135                 140                 145

ctg gcg aac aaa ccg cag gct gag aaa gcc gcc gcg cca gcg gcg ggt     3639
Leu Ala Asn Lys Pro Gln Ala Glu Lys Ala Ala Ala Pro Ala Ala Gly
150                 155                 160                 165

gca gca acg gct cag cag cct gtt gcc aac cgc agc gaa aaa cgt gtt     3687
Ala Ala Thr Ala Gln Gln Pro Val Ala Asn Arg Ser Glu Lys Arg Val
                170                 175                 180

ccg atg acg cgt tta cgt aag cgc gtc gcg gag cgt ctg ctg gaa gcc     3735
Pro Met Thr Arg Leu Arg Lys Arg Val Ala Glu Arg Leu Leu Glu Ala
            185                 190                 195

aag aac agc acc gcc atg ttg acg acc ttc aac gaa atc aac atg aag     3783
Lys Asn Ser Thr Ala Met Leu Thr Thr Phe Asn Glu Ile Asn Met Lys
        200                 205                 210

ccg att atg gat ctg cgt aag cag tac ggc gat gcg ttc gag aag cgt     3831
Pro Ile Met Asp Leu Arg Lys Gln Tyr Gly Asp Ala Phe Glu Lys Arg
    215                 220                 225

cac ggt gtg cgt ctg ggc ttt atg tct ttc tac atc aag gcc gtg gtc     3879
His Gly Val Arg Leu Gly Phe Met Ser Phe Tyr Ile Lys Ala Val Val
230                 235                 240                 245

gaa gcg ctg aag cgt tat cca gaa gtc aac gcc tct atc gat ggc gaa     3927
Glu Ala Leu Lys Arg Tyr Pro Glu Val Asn Ala Ser Ile Asp Gly Glu
                250                 255                 260

gac gtg gtg tac cac aac tat ttc gat gtg agt att gcc gtc tct acg     3975
Asp Val Val Tyr His Asn Tyr Phe Asp Val Ser Ile Ala Val Ser Thr
            265                 270                 275

cca cgc gga ctg gtg acg cct gtc ctg cgt gac gtt gat gcg ctg agc     4023
Pro Arg Gly Leu Val Thr Pro Val Leu Arg Asp Val Asp Ala Leu Ser
```

-continued

```
        280                 285                 290

atg gct gac atc gag aag aaa att aaa gaa ctg gca gtg aaa ggc cgt      4071
Met Ala Asp Ile Glu Lys Lys Ile Lys Glu Leu Ala Val Lys Gly Arg
    295                 300                 305

gac ggc aag ctg acg gtt gac gat ctg acg ggc ggt aac ttt acc atc      4119
Asp Gly Lys Leu Thr Val Asp Asp Leu Thr Gly Gly Asn Phe Thr Ile
310                 315                 320                 325

acc aac ggt ggt gtg ttc ggt tcg ctg atg tct acg cca atc atc aac      4167
Thr Asn Gly Gly Val Phe Gly Ser Leu Met Ser Thr Pro Ile Ile Asn
                330                 335                 340

ccg cca cag agc gcg att ctg ggc atg cac gcc att aaa gat cgt cct      4215
Pro Pro Gln Ser Ala Ile Leu Gly Met His Ala Ile Lys Asp Arg Pro
            345                 350                 355

atg gcg gtc aat ggt cag gtt gtg atc ctg cca atg atg tac ctg gct      4263
Met Ala Val Asn Gly Gln Val Val Ile Leu Pro Met Met Tyr Leu Ala
        360                 365                 370

ctc tcc tac gat cac cgt tta atc gat ggt cgt gaa tct gtc ggc tat      4311
Leu Ser Tyr Asp His Arg Leu Ile Asp Gly Arg Glu Ser Val Gly Tyr
    375                 380                 385

ctg gtc gcg gtg aaa gag atg ctg gaa gat ccg gcg cgt ctg ctg ctg      4359
Leu Val Ala Val Lys Glu Met Leu Glu Asp Pro Ala Arg Leu Leu Leu
390                 395                 400                 405

gat gtc tgattcatca ctgggcacgc gttgcgtgcc caatctcaat actcttttca      4415
Asp Val

gatctgaatg gatagaacat c atg aac tta cac gaa tac cag gct aaa cag      4466
                        Met Asn Leu His Glu Tyr Gln Ala Lys Gln
                          1               5                  10

ctg ttt gca cgg tat ggc atg cca gca ccg acc ggc tac gcc tgt act      4514
Leu Phe Ala Arg Tyr Gly Met Pro Ala Pro Thr Gly Tyr Ala Cys Thr
                15                  20                  25

aca cca cgt gaa gca gaa gaa gcg gca tcg aaa atc ggt gca              4556
Thr Pro Arg Glu Ala Glu Glu Ala Ala Ser Lys Ile Gly Ala
            30                  35                  40


<210> SEQ ID NO 2
<211> LENGTH: 39
<212> TYPE: PRT
<213> ORGANISM: Pantoea ananatis

<400> SEQUENCE: 2

Ala Phe Ser Val Phe Arg Cys His Ser Ile Met Asn Cys Val Ser Val
  1               5                  10                  15

Cys Pro Lys Gly Leu Asn Pro Thr Arg Ala Ile Gly His Ile Lys Ser
            20                  25                  30

Met Leu Leu Gln Arg Ser Ala
        35


<210> SEQ ID NO 3
<211> LENGTH: 935
<212> TYPE: PRT
<213> ORGANISM: Pantoea ananatis

<400> SEQUENCE: 3

Met Gln Asn Ser Ala Met Lys Pro Trp Leu Asp Ser Ser Trp Leu Ala
  1               5                  10                  15

Gly Ala Asn Gln Ser Tyr Ile Glu Gln Leu Tyr Glu Asp Phe Leu Thr
            20                  25                  30

Asp Pro Asp Ser Val Asp Ala Val Trp Arg Ser Met Phe Gln Gln Leu
        35                  40                  45
```

-continued

```
Pro Gly Thr Gly Val Lys Pro Glu Gln Phe His Ser Ala Thr Arg Glu
     50                  55                  60

Tyr Phe Arg Arg Leu Ala Lys Asp Ala Ser Arg Tyr Thr Ser Ser Val
 65                  70                  75                  80

Thr Asp Pro Ala Thr Asn Ser Lys Gln Val Lys Val Leu Gln Leu Ile
                 85                  90                  95

Asn Ala Phe Arg Phe Arg Gly His Gln Glu Ala Asn Leu Asp Pro Leu
            100                 105                 110

Gly Leu Trp Lys Gln Asp Arg Val Ala Asp Leu Asp Pro Ala Phe His
        115                 120                 125

Asp Leu Thr Asp Ala Asp Phe Gln Glu Ser Phe Asn Val Gly Ser Phe
    130                 135                 140

Ala Ile Gly Lys Glu Thr Met Lys Leu Ala Asp Leu Phe Asp Ala Leu
145                 150                 155                 160

Lys Gln Thr Tyr Cys Gly Ser Ile Gly Ala Glu Tyr Met His Ile Asn
                165                 170                 175

Asn Thr Glu Glu Lys Arg Trp Ile Gln Gln Arg Ile Glu Ser Gly Ala
            180                 185                 190

Ser Gln Thr Ser Phe Ser Gly Glu Glu Lys Lys Gly Phe Leu Lys Glu
        195                 200                 205

Leu Thr Ala Ala Glu Gly Leu Glu Lys Tyr Leu Gly Ala Lys Phe Pro
    210                 215                 220

Gly Ala Lys Arg Phe Ser Leu Glu Gly Gly Asp Ala Leu Val Pro Met
225                 230                 235                 240

Leu Arg Glu Met Ile Arg His Ala Gly Lys Ser Gly Thr Arg Glu Val
                245                 250                 255

Val Leu Gly Met Ala His Arg Gly Arg Leu Asn Val Leu Ile Asn Val
            260                 265                 270

Leu Gly Lys Lys Pro Gln Asp Leu Phe Asp Glu Phe Ser Gly Lys His
        275                 280                 285

Lys Glu His Leu Gly Thr Gly Asp Val Lys Tyr His Met Gly Phe Ser
    290                 295                 300

Ser Asp Ile Glu Thr Glu Gly Gly Leu Val His Leu Ala Leu Ala Phe
305                 310                 315                 320

Asn Pro Ser His Leu Glu Ile Val Ser Pro Val Val Met Gly Ser Val
                325                 330                 335

Arg Ala Arg Leu Asp Arg Leu Ala Glu Pro Val Ser Asn Lys Val Leu
            340                 345                 350

Pro Ile Thr Ile His Gly Asp Ala Ala Val Ile Gly Gln Gly Val Val
        355                 360                 365

Gln Glu Thr Leu Asn Met Ser Gln Ala Arg Gly Tyr Glu Val Gly Gly
    370                 375                 380

Thr Val Arg Ile Val Ile Asn Asn Gln Val Gly Phe Thr Thr Ser Asn
385                 390                 395                 400

Pro Lys Asp Ala Arg Ser Thr Pro Tyr Cys Thr Asp Ile Gly Lys Met
                405                 410                 415

Val Leu Ala Pro Ile Phe His Val Asn Ala Asp Asp Pro Glu Ala Val
            420                 425                 430

Ala Phe Val Thr Arg Leu Ala Leu Asp Tyr Arg Asn Thr Phe Lys Arg
        435                 440                 445

Asp Val Phe Ile Asp Leu Val Cys Tyr Arg Arg His Gly His Asn Glu
    450                 455                 460

Ala Asp Glu Pro Ser Ala Thr Gln Pro Leu Met Tyr Gln Lys Ile Lys
```

-continued

```
465                 470                 475                 480

Lys His Pro Thr Pro Arg Lys Ile Tyr Ala Asp Arg Leu Glu Gly Glu
                485                 490                 495

Gly Val Ala Ser Gln Glu Asp Ala Thr Glu Met Val Asn Leu Tyr Arg
            500                 505                 510

Asp Ala Leu Asp Ala Gly Glu Cys Val Val Pro Glu Trp Arg Pro Met
        515                 520                 525

Ser Leu His Ser Phe Thr Trp Ser Pro Tyr Leu Asn His Glu Trp Asp
    530                 535                 540

Glu Pro Tyr Pro Ala Gln Val Asp Met Lys Arg Leu Lys Glu Leu Ala
545                 550                 555                 560

Leu Arg Ile Ser Gln Val Pro Glu Gln Ile Glu Val Gln Ser Arg Val
                565                 570                 575

Ala Lys Ile Tyr Asn Asp Arg Lys Leu Met Ala Glu Gly Glu Lys Ala
            580                 585                 590

Phe Asp Trp Gly Gly Ala Glu Asn Leu Ala Tyr Ala Thr Leu Val Asp
        595                 600                 605

Glu Gly Ile Pro Val Arg Leu Ser Gly Glu Asp Ser Gly Arg Gly Thr
    610                 615                 620

Phe Phe His Arg His Ala Val Val His Asn Gln Ala Asn Gly Ser Thr
625                 630                 635                 640

Tyr Thr Pro Leu His His Ile His Asn Ser Gln Gly Glu Phe Lys Val
                645                 650                 655

Trp Asp Ser Val Leu Ser Glu Glu Ala Val Leu Ala Phe Glu Tyr Gly
            660                 665                 670

Tyr Ala Thr Ala Glu Pro Arg Val Leu Thr Ile Trp Glu Ala Gln Phe
        675                 680                 685

Gly Asp Phe Ala Asn Gly Ala Gln Val Val Ile Asp Gln Phe Ile Ser
    690                 695                 700

Ser Gly Glu Gln Lys Trp Gly Arg Met Cys Gly Leu Val Met Leu Leu
705                 710                 715                 720

Pro His Gly Tyr Glu Gly Gln Gly Pro Glu His Ser Ser Ala Arg Leu
                725                 730                 735

Glu Arg Tyr Leu Gln Leu Cys Ala Glu Gln Asn Met Gln Val Cys Val
            740                 745                 750

Pro Ser Thr Pro Ala Gln Val Tyr His Met Leu Arg Arg Gln Ala Leu
        755                 760                 765

Arg Gly Met Arg Arg Pro Leu Val Val Met Ser Pro Lys Ser Leu Leu
    770                 775                 780

Arg His Pro Leu Ala Ile Ser Ser Leu Asp Glu Leu Ala Asn Gly Ser
785                 790                 795                 800

Phe Gln Pro Ala Ile Gly Glu Ile Asp Asp Leu Asp Pro Gln Gly Val
                805                 810                 815

Lys Arg Val Val Leu Cys Ser Gly Lys Val Tyr Tyr Asp Leu Leu Glu
            820                 825                 830

Gln Arg Arg Lys Asp Glu Lys Thr Asp Val Ala Ile Val Arg Ile Glu
        835                 840                 845

Gln Leu Tyr Pro Phe Pro His Gln Ala Val Gln Glu Ala Leu Lys Ala
    850                 855                 860

Tyr Ser His Val Gln Asp Phe Val Trp Cys Gln Glu Glu Pro Leu Asn
865                 870                 875                 880

Gln Gly Ala Trp Tyr Cys Ser Gln His His Phe Arg Asp Val Val Pro
                885                 890                 895
```

-continued

```
Phe Gly Ala Thr Leu Arg Tyr Ala Gly Arg Pro Ala Ser Ala Ser Pro
            900                 905                 910

Ala Val Gly Tyr Met Ser Val His Gln Gln Gln Gln Gln Asp Leu Val
        915                 920                 925

Asn Asp Ala Leu Asn Val Asn
    930                 935


<210> SEQ ID NO 4
<211> LENGTH: 407
<212> TYPE: PRT
<213> ORGANISM: Pantoea ananatis

<400> SEQUENCE: 4

Met Ser Ser Val Asp Ile Leu Val Pro Asp Leu Pro Glu Ser Val Ala
  1               5                  10                  15

Asp Ala Thr Val Ala Thr Trp His Lys Lys Pro Gly Asp Ala Val Ser
             20                  25                  30

Arg Asp Glu Val Ile Val Glu Ile Glu Thr Asp Lys Val Val Leu Glu
         35                  40                  45

Val Pro Ala Ser Ala Asp Gly Val Leu Glu Ala Val Leu Glu Asp Glu
     50                  55                  60

Gly Ala Thr Val Thr Ser Arg Gln Ile Leu Gly Arg Leu Lys Glu Gly
 65                  70                  75                  80

Asn Ser Ala Gly Lys Glu Ser Ser Ala Lys Ala Glu Ser Asn Asp Thr
                 85                  90                  95

Thr Pro Ala Gln Arg Gln Thr Ala Ser Leu Glu Glu Glu Ser Ser Asp
            100                 105                 110

Ala Leu Ser Pro Ala Ile Arg Arg Leu Ile Ala Glu His Asn Leu Asp
        115                 120                 125

Ala Ala Gln Ile Lys Gly Thr Gly Val Gly Gly Arg Leu Thr Arg Glu
    130                 135                 140

Asp Val Glu Lys His Leu Ala Asn Lys Pro Gln Ala Glu Lys Ala Ala
145                 150                 155                 160

Ala Pro Ala Ala Gly Ala Ala Thr Ala Gln Gln Pro Val Ala Asn Arg
                165                 170                 175

Ser Glu Lys Arg Val Pro Met Thr Arg Leu Arg Lys Arg Val Ala Glu
            180                 185                 190

Arg Leu Leu Glu Ala Lys Asn Ser Thr Ala Met Leu Thr Thr Phe Asn
        195                 200                 205

Glu Ile Asn Met Lys Pro Ile Met Asp Leu Arg Lys Gln Tyr Gly Asp
    210                 215                 220

Ala Phe Glu Lys Arg His Gly Val Arg Leu Gly Phe Met Ser Phe Tyr
225                 230                 235                 240

Ile Lys Ala Val Val Glu Ala Leu Lys Arg Tyr Pro Glu Val Asn Ala
                245                 250                 255

Ser Ile Asp Gly Glu Asp Val Val Tyr His Asn Tyr Phe Asp Val Ser
            260                 265                 270

Ile Ala Val Ser Thr Pro Arg Gly Leu Val Thr Pro Val Leu Arg Asp
        275                 280                 285

Val Asp Ala Leu Ser Met Ala Asp Ile Glu Lys Lys Ile Lys Glu Leu
    290                 295                 300

Ala Val Lys Gly Arg Asp Gly Lys Leu Thr Val Asp Asp Leu Thr Gly
305                 310                 315                 320

Gly Asn Phe Thr Ile Thr Asn Gly Gly Val Phe Gly Ser Leu Met Ser
```

-continued

```
                325                 330                 335

Thr Pro Ile Ile Asn Pro Pro Gln Ser Ala Ile Leu Gly Met His Ala
            340                 345                 350

Ile Lys Asp Arg Pro Met Ala Val Asn Gly Gln Val Val Ile Leu Pro
        355                 360                 365

Met Met Tyr Leu Ala Leu Ser Tyr Asp His Arg Leu Ile Asp Gly Arg
    370                 375                 380

Glu Ser Val Gly Tyr Leu Val Ala Val Lys Glu Met Leu Glu Asp Pro
385                 390                 395                 400

Ala Arg Leu Leu Leu Asp Val
                405


<210> SEQ ID NO 5
<211> LENGTH: 40
<212> TYPE: PRT
<213> ORGANISM: Pantoea ananatis

<400> SEQUENCE: 5

Met Asn Leu His Glu Tyr Gln Ala Lys Gln Leu Phe Ala Arg Tyr Gly
  1               5                  10                  15

Met Pro Ala Pro Thr Gly Tyr Ala Cys Thr Thr Pro Arg Glu Ala Glu
             20                  25                  30

Glu Ala Ala Ser Lys Ile Gly Ala
         35                  40


<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6

gtcgacaata gccygaatct gttctggtcg                                      30


<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7

aagcttatcg acgctcccct ccccaccgtt                                      30


<210> SEQ ID NO 8
<211> LENGTH: 16214
<212> TYPE: DNA
<213> ORGANISM: Artificial Sequence
<220> FEATURE:
<223> OTHER INFORMATION: plasmid RSFCPG

<400> SEQUENCE: 8

gaattccgcc agaaccttca tcagcagcat aaacaggtgc agtgaacagc agagatacgg      60

ccagtgcggc caatgttttt tgtcctttaa acataacaga gtcctttaag gatatagaat     120

aggggtatag ctacgccaga atatcgtatt tgattattgc tagtttttag ttttgcttaa     180

aaaatattgt tagttttatt aaattggaaa actaaattat tggtatcatg aattgttgta     240

tgatgataaa tataggggg atatgataga cgtcattttc atagggttat aaaatgcgac     300

taccatgaag tttttaattc aaagtattgg gttgctgata atttgagctg ttctattctt     360
```

-continued

```
tttaaatatc tatataggtc tgttaatgga ttttattttt acaagttttt tgtgtttagg    420
catataaaaa tcaagcccgc catatgaacg gcgggttaaa atatttacaa cttagcaatc    480
gaaccattaa cgcttgatat cgcttttaaa gtcgcgtttt tcatatcctg tatacagctg    540
acgcggacgg gcaatcttca taccgtcact gtgcatttcg ctccagtggg cgatccagcc    600
aacggtacgt gccattgcga aaatgacggt gaacatggaa gacggaatac ccatcgcttt    660
caggatgata ccagagtaga aatcgacgtt cgggtacagt ttcttctcga taaagtacgg    720
gtcgttcagc gcgatgtttt ccagctccat agccacttcc agcaggtcat ccttcgtgcc    780
cagctctttc agcacttcat ggcaggtttc acgcattacg gtggcgcgcg ggtcgtaatt    840
tttgtacacg cggtgaccga agcccatcag gcggaaagaa tcatttttgt ctttcgcacg    900
acgaaaaaat tccggaatgt gtttaacgga gctgatttct tccagcattt tcagcgccgc    960
ttcgttagca ccgccgtgcg caggtcccca cagtgaagca atacctgctg cgatacaggc   1020
aaacgggttc gcacccgaag agccagcggt acgcacggtg gaggtagagg cgttctgttc   1080
atggtcagcg tgcaggatca gaatacggtc catagcacgt tccagaatcg gattaacttc   1140
atacggttcg cacggcgtgg agaacatcat attcaggaag ttaccggcgt aggagagatc   1200
gttgcgcggg taaacaaatg gctgaccaat ggaatacttg taacacatcg cggccatggt   1260
cggcattttc gacagcaggc ggaacgcggc aatttcacgg tgacgaggat tgttaacatc   1320
cagcgagtcg tgatagaacg ccgccagcgc gccggtaata ccacacatga ctgccattgg   1380
atgcgagtcg cgacggaaag catggaacag acgggtaatc tgctcgtgga tcatggtatg   1440
acgggtcacc gtagttttaa attcgtcata ctgttcctga gtcggttttt caccattcag   1500
caggatgtaa caaacttcca ggtagttaga atcggtcgcc agctgatcga tcgggaaacc   1560
gcggtgcagc aaaatacctt catcaccatc aataaaagta attttagatt cgcaggatgc   1620
ggttgaagtg aagcctgggt caaaggtgaa cacacctttt gaaccgagag tacggatatc   1680
aataacatct tgacccagcg tgcctttcag cacatccagt tcaacagctg tatccccgtt   1740
gagggtgagt tttgcttttg tatcagccat ttaaggtctc cttagcgcct tattgcgtaa   1800
gactgccgga acttaaattt gccttcgcac atcaacctgg ctttacccgt tttttatttg   1860
gctcgccgct ctgtgaaaga ggggaaaacc tgggtacaga gctctgggcg cttgcaggta   1920
aaggatccat tgatgacgaa taaatggcga atcaagtact tagcaatccg aattattaaa   1980
cttgtctacc actaataact gtcccgaatg aattggtcaa tactccacac tgttacataa   2040
gttaatctta ggtgaaatac cgacttcata acttttacgc attatatgct tttcctggta   2100
atgtttgtaa caactttgtt gaatgattgt caaattagat gattaaaaat taaataaatg   2160
ttgttatcgt gacctggatc actgttcagg ataaaacccg acaaactata tgtaggttaa   2220
ttgtaatgat tttgtgaaca gcctatactg ccgccagtct ccggaacacc ctgcaatccc   2280
gagccaccca gcgttgtaac gtgtcgtttt cgcatctgga agcagtgttt tgcatgacgc   2340
gcagttatag aaaggacgct gtctgacccg caagcagacc ggaggaagga aatcccgacg   2400
tcggggatcc tctagagctt tagcgtctga ggttatcgca atttggttat gagattactc   2460
tcgttattaa tttgctttcc tgggtcattt ttttcttgct taccgtcaca ttcttgatgg   2520
tatagtcgaa aactgcaaaa gcacatgaca taaacaacat aagcacaatc gtattaatat   2580
ataagggttt tatatctatg gatcagacat attctctgga gtcattcctc aaccatgtcc   2640
aaaagcgcga cccgaatcaa accgagttcg cgcaagccgt tcgtgaagta atgaccacac   2700
```

-continued

```
tctggccttt tcttgaacaa aatccaaaat atcgccagat gtcattactg gagcgtctgg   2760
ttgaaccgga gcgcgtgatc cagtttcgcg tggtatgggt tgatgatcgc aaccagatac   2820
aggtcaaccg tgcatggcgt gtgcagttca gctctgccat cggcccgtac aaaggcggta   2880
tgcgcttcca tccgtcagtt aacctttcca ttctcaaatt cctcggcttt gaacaaacct   2940
tcaaaaatgc cctgactact ctgccgatgg gcggtggtaa aggcggcagc gatttcgatc   3000
cgaaaggaaa aagcgaaggt gaagtgatgc gtttttgcca ggcgctgatg actgaactgt   3060
atcgccacct gggcgcggat accgacgttc cggcaggtga tatcggggtt ggtggtcgtg   3120
aagtcggctt tatggcgggg atgatgaaaa agctctccaa caataccgcc tgcgtcttca   3180
ccggtaaggg cctttcattt ggcggcagtc ttattcgccc ggaagctacc ggctacggtc   3240
tggtttattt cacagaagca atgctaaaac gccacggtat gggttttgaa gggatgcgcg   3300
tttccgtttc tggctccggc aacgtcgccc agtacgctat cgaaaaagcg atggaatttg   3360
gtgctcgtgt gatcactgcg tcagactcca gcggcactgt agttgatgaa agcggattca   3420
cgaaagagaa actggcacgt cttatcgaaa tcaaagccag ccgcgatggt cgagtggcag   3480
attacgccaa agaatttggt ctggtctatc tcgaaggcca acagccgtgg tctctaccgg   3540
ttgatatcgc cctgccttgc gccacccaga atgaactgga tgttgacgcc gcgcatcagc   3600
ttatcgctaa tggcgttaaa gccgtcgccg aaggggcaaa tatgccgacc accatcgaag   3660
cgactgaact gttccagcag gcaggcgtac tatttgcacc gggtaaagcg gctaatgctg   3720
gtggcgtcgc tacatcgggc ctggaaatgc cacaaaacgc tgcgcgcctg ggctggaaag   3780
ccgagaaagt tgacgcacgt ttgcatcaca tcatgctgga tatccaccat gcctgtgttg   3840
agcatggtgg tgaaggtgag caaaccaact acgtgcaggg cgcgaacatt gccggttttg   3900
tgaaggttgc cgatgcgatg ctggcgcagg gtgtgattta agttgtaaat gcctgatggc   3960
gctacgctta tcaggcctac aaatgggcac aattcattgc agttacgctc taatgtaggc   4020
cgggcaagcg cagcgccccc ggcaaaattt caggcgttta tgagtattta acggatgatg   4080
ctccccacgg aacatttctt atgggccaac ggcatttctt actgtagtgc tcccaaaact   4140
gcttgtcgta acgataacac gcttcaagtt cagcatccgt taactttctg cggactcacg   4200
cgcgcagcac tatgccagta aagaaatccc atttgactat ttttttgata atcttcttcg   4260
ctttcgaaca actcgtgcgc ctttcgagaa gctagagtcg actcgccaat caccagcact   4320
aaagtgcgcg gttcgttacc cgattcatct ttgaaattag ccagtggcgg caaggcatta   4380
ttttcattca gtaactttgt tagcgagttt agttgctgac gatactgata atagccggtc   4440
aggaattgcc acggtgcggc aggctccata cgcgaggcca ggttatccaa cgttttctca   4500
aacggcttgt ttttgataaa cgtattcatg gcgatcggat gcagaatcaa gccataaagc   4560
agggcaaaag agacaacata acgccacggc tttggaatat agaccgggcg caggcgtgtc   4620
cacagcagaa ctgccaccgc cgtataggcc agcgcgataa gcacaatttt caggctgaaa   4680
tactggctta aatactcgct ggcttcgttg gtgttggttt cgaacatcac aaacagaacg   4740
ctctgcgaga actcctgacc gtagatgacg tagtagcaca gcgccgccag agaggccgcc   4800
catagcacca cgccgattac tgcggcaata attttaatcc gcttcggaaa gaggaatacc   4860
gggatcaacc acagcgaact gaataacagc gagtcgcgaa tgccgttagt gccactataa   4920
ccactgatgt aaataatggc ctgtagcaga gtagagaaaa accaaaagta gagcagtgcc   4980
caacccaggg ctttccagct aaaaagaggt ttagcctgga cttctgtgga atgcatagta   5040
agaacctgtc ttgaaaaaat atcgccgaat gtaacgacaa ttccttaagg atatctgaag   5100
```

-continued

```
gtatattcag aatttgaata aaatgcagac agaaatatat tgaaaacgag ggtgttagaa   5160
cagaagtatt tcagaaaacc ctcgcgcaaa agcacgaggg tttgcagaag aggaagatta   5220
gccggtatta cgcatacctg ccgcaatccc ggcaatagtg accattaacg cttgttcgac   5280
gcgaggatcc ggttcctggc cttctttttc tgcctggcgg gagcggtgca gcaactcggc   5340
ctgcaatacg ttcagcgggt cggtgtaaat attccgtagc tgaatagact ctgcaatcca   5400
cggcagatcg gccatcagat gggaatcgtt ggcaatcgcc agcaccactt tgatgtcttc   5460
ttcttgcagg ttgcgtaact ctttacctaa cggccacagt gctttgtcta ccaggcgttg   5520
gtcatagtat tccgccagcc acaggtctgc tttggcgaag accatctcca gcatgccgag   5580
acgcgtcgag aagaatggcc aatcgcggca catagcctcc agctcgctct gtttgccgtc   5640
ttcgaccact ttttgcagcg ccgtacctgc acccagccag gcggggagca tcagacggtt   5700
ttgcgtccag gcgaagatcc acggaatggc gcgtagtgac tcgacgccgc cggttgggcg   5760
acgtttcgcc ggacgtgaac ccaacggcag tttgcccagt tcttgttccg gcgtagcgga   5820
gcggaagtaa ggcacaaaat ctttgttttc acgtacgtag ccgcggtaga catcgcagga   5880
gatgactgac agttcatcca taatgcgacg ccagctctct ttcggctccg gcggtggcag   5940
caggttggct tccagaatcg ccccggtata aagcgacagg ctgctgacgg tgatttctgg   6000
cagaccatat ttaaagcgga tcatctcgcc ctgttcggtt acgcgcaggc cgcctttcag   6060
gcttcctggc ggttgtgaca gcagcgccgc atgagcaggt gcgccgccgc gaccaatgga   6120
accgccgcga ccgtggaaca acgtcagctc aatacccgct tttcgcaggt tttgattaa    6180
tgcatcctgt gcctgatatt gcgcccagga agctgccatc actcccgcat cttttgctga   6240
gtcggaatag ccaatcatca ccatctgttt gccctgaatc aggccacgat accagtcaat   6300
attgagcagc tgggtcatga catcgttggc gttgttcaga tcatcgaggg tttcaaacag   6360
cggagcaacc ggcatcgcaa acccgatacc cgcttctttc agcagcaggt ggacagccag   6420
tacgtcggac ggcgttttcg ccatcgagat cacgtaggcg gcaatggagc cttgcggtgc   6480
ttcggcaatc acctggcagg tatcgagcac ttcgcgcgtt tcggcgcttg gttgccagtt   6540
gcgcggcaga agcggacgtt tggagttcag ttcgcggatc aggaacgcct gtttgtcggc   6600
ctctgaccag ctttcgtagt cgccgatacc gaggtagcgg gtcagctcgc ccagcgcttc   6660
ggtatgacgc gtgctctcct gacggatatc aatacggacc agcggtacgc cgaaacattt   6720
cacgcggcgc agggtgtcga gcagatcgcc gttggcgata atacccatgc cacacgcctg   6780
aagtgactgg tagcaagcgt agagcggttc ccacagttct tcgttttgtg tcagcaggcc   6840
ttctggtttt ggcagttctt cgcctttcag gcgcgcttcc agccatgcct gtgtcgccat   6900
caggcgagaa cgcaggtttt tcatcagata gcgatacggt tctgcggcac cttcttcgcc   6960
aaccagcgcc agcagttcag ggtcgcttc  aaccatcgac agttcagaaa ccagcacctg   7020
aatatctttc aggaacaaat cggtggcttt ccagcggctg agtagcagga cgtggcgggt   7080
gatatcggca gtgacgttcg ggttgccgtc gcggtcgccg cccatccacg aagtaaaacg   7140
gaccggaaca aattcgacgg gcagtttgta gccgaggttc tcttccagtt gttcgttcag   7200
ttcgcgcagg taatttggta cgccttgcca caggctgttt tccactacgg caaagcccca   7260
tttggcttca tctaccgggc ttggacgcag cttacggatt tcatcggtat gccatgactg   7320
ggcgatcaac tggcgcaggc gacgcatcag ctggttgtgt tcgtagtcag cgatatcttt   7380
gttatcgagc tgttttaaac aggcgttcac ttccaccatt ttgtggatca gtgtacgacg   7440
```

-continued

```
ggtaatttcg gttgggtgag ccgtgaggac cagttccagc gacagcgatt ccactgcttt   7500
tttgatggtg tcttcgctca gttccggctg gtttttcagt ttacgcaggg tgcgggcgat   7560
cacttccggg ttgctggcag cttcgccttt cggcgaaatg ctgtggtatt gctcggcggt   7620
gttggccagg ttcaggaact gactaaacgc acgcgcaacg ggcagcagct cgtcgttcga   7680
caaattttgt aaggtggtga gcaactcctg gcggttagca tcattgccag cgcgtgaaga   7740
tttcgacaac ttacggatag tttctacgcg ttcaagaatg tgttctccca acgcatcctt   7800
gatggtttct cccagcactt tgccgagcat actgacatta ctacgcaatg cggaatattg   7860
ttcgttcata ttaccccaga caccccatct tatcgtttga tagccctgta tccttcacgt   7920
cgcattggcg cgaatatgct cgggctttgc ttttcgtcgt cttttataaa gccacgtaaa   7980
agcggtgacg tcaaatgctg cgaaatcgct tcagcaaacg aataaatagc aggaatttac   8040
gtcattaaat tcacgacgct ttaaataagc gtaacttatg gaaatgttaa aaaatcgccc   8100
caagtaacac caaaggtgta ggtcggataa gatgcgcaag tatcgcatcc gacattattg   8160
cggcactgga gtttggcaac agtgccggat gcggcgcgag cgccttatcc ggcctacagt   8220
tgggcatcgt ttgagtcact gtcggtcgga taagatgcgc aagtatcgca tccgacatta   8280
ttgcggcact ggagtttggc aacagtgccg gatgcggcgc gagcgcctta tccggcctac   8340
ggttgggcat cgtttgagtc actgtaggtc ggataagatg cgcaagcatc gcatccgaca   8400
ttattgcggc actggagttt ggcaacagcg ccggatgcgg cgcgagcgcc ttatccggcc   8460
tacgttttaa tgccagcaaa aatggtgaat tacctgggtt atcagttcgc gggtgggctt   8520
gataaaccgt gtttccagat attcatcagg ttgatgagcc tgattaattg agccaggccc   8580
caacaccagc gtcgggcata acgtttgaat aaacggcgct tcggtacagt agttcaccac   8640
ttcggttttt gctccgagca atttctcaac cacttcaacc agttgatgat tcggtgggca   8700
ttcatagcca gggatcggcg gatgcagctc gtcgacctgc aggagcagaa gagcatacat   8760
ctggaagcaa agccaggaaa gcggcctatg gagctgtgcg gcagcgctca gtaggcaatt   8820
tttcaaaata ttgttaagcc ttttctgagc atggtatttt tcatggtatt accaattagc   8880
aggaaaataa gccattgaat ataaaagata aaaatgtctt gtttacaata gagtgggggg   8940
ggtcagcctg ccgccttggg ccgggtgatg tcgtacttgc ccgccgcgaa ctcggttacc   9000
gtccagccca gcgcgaccag ctccggcaac gcctcgcgca cccgctggcg gcgcttgcgc   9060
atggtcgaac cactggcctc tgacggccag acatagccgc acaaggtatc tatggaagcc   9120
ttgccggttt tgccggggtc gatccagcca cacagccgct ggtgcagcag gcgggcggtt   9180
tcgctgtcca gcgcccgcac ctcgtccatg ctgatgcgca catgctggcc gccacccatg   9240
acggcctgcg cgatcaaggg gttcagggcc acgtacaggc gcccgtccgc ctcgtcgctg   9300
gcgtactccg acagcagccg aaacccctgc cgcttgcggc cattctgggc gatgatggat   9360
accttccaaa ggcgctcgat gcagtcctgt atgtgcttga gcgccccacc actatcgacc   9420
tctgccccga tttcctttgc cagcgcccga tagctacctt tgaccacatg gcattcagcg   9480
gtgacggcct cccacttggg ttccaggaac agccggagct gccgtccgcc ttcggtcttg   9540
ggttccgggc caagcactag gccattaggc ccagccatgg ccaccagccc ttgcaggatg   9600
cgcagatcat cagcgcccag cggctccggg ccgctgaact cgatccgctt gccgtcgccg   9660
tagtcatacg tcacgtccag cttgctgcgc ttgcgctcgc cccgcttgag ggcacggaac   9720
aggccggggg ccagacagtg cgccgggtcg tgccggacgt ggctgaggct gtgcttgttc   9780
ttaggcttca ccacggggca ccccccttgct cttgcgctgc ctctccagca cggcgggctt   9840
```

-continued

```
gagcaccccg ccgtcatgcc gcctgaacca ccgatcagcg aacggtgcgc catagttggc   9900
cttgctcaca ccgaagcgga cgaagaaccg gcgctggtcg tcgtccacac cccattcctc   9960
ggcctcggcg ctggtcatgc tcgacaggta ggactgccag cggatgttat cgaccagtac  10020
cgagctgccc cggctggcct gctgctggtc gcctgcgccc atcatggccg cgcccttgct  10080
ggcatggtgc aggaacacga tagagcaccc ggtatcggcg gcgatggcct ccatgcgacc  10140
gatgacctgg gccatggggc cgctggcgtt ttcttcctcg atgtggaacc ggcgcagcgt  10200
gtccagcacc atcaggcggc ggccctcggc ggcgcgcttg aggccgtcga accactccgg  10260
ggccatgatg ttgggcaggc tgccgatcag cggctggatc agcaggccgt cagccacggc  10320
ttgccgttcc tcggcgctga ggtgcgcccc aagggcgtgc aggcggtgat gaatggcggt  10380
gggcgggtct tcggcgggca ggtagatcac cgggccggtg ggcagttcgc ccacctccag  10440
cagatccggc ccgcctgcaa tctgtgcggc cagttgcagg gccagcatgg atttaccggc  10500
accaccgggc gacaccagcg ccccgaccgt accggccacc atgttgggca aaacgtagtc  10560
cagcggtggc ggcgctgctg cgaacgcctc cagaatattg ataggcttat gggtagccat  10620
tgattgcctc ctttgcaggc agttggtggt taggcgctgg cggggtcact acccccgccc  10680
tgcgccgctc tgagttcttc caggcactcg cgcagcgcct cgtattcgtc gtcggtcagc  10740
cagaacttgc gctgacgcat ccctttggcc ttcatgcgct cggcatatcg cgcttggcgt  10800
acagcgtcag ggctggccag caggtcgccg gtctgcttgt ccttttggtc tttcatatca  10860
gtcaccgaga aacttgccgg ggccgaaagg cttgtcttcg cggaacaagg acaaggtgca  10920
gccgtcaagg ttaaggctgg ccatatcagc gactgaaaag cggccagcct cggccttgtt  10980
tgacgtataa ccaaagccac cgggcaacca atagcccttg tcacttttga tcaggtagac  11040
cgaccctgaa gcgctttttt cgtattccat aaaacccccct tctgtgcgtg agtactcata  11100
gtataacagg cgtgagtacc aacgcaagca ctacatgctg aaatctggcc cgcccctgtc  11160
catgcctcgc tggcggggtg ccggtgcccg tgccagctcg gcccgcgcaa gctggacgct  11220
gggcagaccc atgaccttgc tgacggtgcg ctcgatgtaa tccgcttcgt ggccgggctt  11280
gcgctctgcc agcgctgggc tggcctcggc catggccttg ccgatttcct cggcactgcg  11340
gccccggctg gccagcttct gcgcggcgat aaagtcgcac ttgctgaggt catcaccgaa  11400
gcgcttgacc agcccggcca tctcgctgcg gtactcgtcc agcgccgtgc gccggtggcg  11460
gctaagctgc cgctcgggca gttcgaggct ggccagcctg cgggccttct cctgctgccg  11520
ctgggcctgc tcgatctgct ggccagcctg ctgcaccagc gccgggccag cggtggcggt  11580
cttgcccttg gattcacgca gcagcaccca cggctgataa ccggcgcggg tggtgtgctt  11640
gtccttgcgg ttggtgaagc ccgccaagcg gccatagtgg cggctgtcgg cgctggccgg  11700
gtcggcgtcg tactcgctgg ccagcgtccg ggcaatctgc cccccgaagtt caccgcctgc  11760
ggcgtcggcc accttgaccc atgcctgata gttcttcggg ctggtttcca ctaccagggc  11820
aggctcccgg ccctcggctt tcatgtcatc caggtcaaac tcgctgaggt cgtccaccag  11880
caccagacca tgccgctcct gctcggcggg cctgatatac acgtcattgc cctgggcatt  11940
catccgcttg agccatggcg tgttctggag cacttcggcg gctgaccatt cccggttcat  12000
catctggccg gtggtggcgt ccctgacgcc gatatcgaag cgctcacagc ccatggcctt  12060
gagctgtcgg cctatggcct gcaaagtcct gtcgttcttc atcgggccac caagcgcagc  12120
cagatcgagc cgtcctcggt tgtcagtggc gtcaggtcga gcaagagcaa cgatgcgatc  12180
```

-continued

```
agcagcacca ccgtaggcat catggaagcc agcatcacgg ttagccatag cttccagtgc  12240
cacccccgcg acgcgctccg ggcgctctgc gcggcgctgc tcacctcggc ggctacctcc  12300
cgcaactctt tggccagctc cacccatgcc gcccctgtct ggcgctgggc tttcagccac  12360
tccgccgcct gcgcctcgct ggcctgctgg gtctggctca tgacctgccg ggcttcgtcg  12420
gccagtgtcg ccatgctctg ggccagcggt tcgatctgct ccgctaactc gttgatgcct  12480
ctggatttct tcactctgtc gattgcgttc atggtctatt gcctcccggt attcctgtaa  12540
gtcgatgatc tgggcgttgg cggtgtcgat gttcagggcc acgtctgccc ggtcggtgcg  12600
gatgccccgg ccttccatct ccaccacgtt cggccccagg tgaacaccgg gcaggcgctc  12660
gatgccctgc gcctcaagtg ttctgtggtc aatgcgggcg tcgtggccag cccgctctaa  12720
tgcccggttg gcatggtcgg cccatgcctc gcgggtctgc tcaagccatg ccttgggctt  12780
gagcgcttcg gtcttctgtg ccccgccctt ctccggggtc ttgccgttgt accgcttgaa  12840
ccactgagcg gcgggccgct cgatgccgtc attgatccgc tcggagatca tcaggtggca  12900
gtgcgggttc tcgccgccac cggcatggat ggccagcgta tacggcaggc gctcggcacc  12960
ggtcaggtgc tgggcgaact cggacgccag cgccttctgc tggtcgaggg tcagctcgac  13020
cggcagggca aattcgacct ccttgaacag ccgcccattg gcgcgttcat acaggtcggc  13080
agcatcccag tagtcggcgg gccgctcgac gaactccggc atgtgcccgg attcggcgtg  13140
caagacttca tccatgtcgc gggcatactt gccttcgcgc tggatgtagt cggccttggc  13200
cctggccgat tggccgcccg acctgctgcc ggttttcgcc gtaaggtgat aaatcgccat  13260
gctgcctcgc tgttgctttt gcttttcggc tccatgcaat ggccctcgga gagcgcaccg  13320
cccgaagggt ggccgttagg ccagtttctc gaagagaaac cggtaagtgc gccctcccct  13380
acaaagtagg gtcgggattg ccgccgctgt gcctccatga tagcctacga gacagcacat  13440
taacaatggg gtgtcaagat ggttaagggg agcaacaagg cggcggatcg gctggccaag  13500
ctcgaagaac aacgagcgcg aatcaatgcc gaaattcagc gggtgcgggc aagggaacag  13560
cagcaagagc gcaagaacga aacaaggcgc aaggtgctgg tgggggccat gattttggcc  13620
aaggtgaaca gcagcgagtg gccggaggat cggctcatgg cggcaatgga tgcgtacctt  13680
gaacgcgacc acgaccgcgc cttgttcggt ctgccgccac gccagaagga tgagccgggc  13740
tgaatgatcg accgagacag gccctgcggg gctgcacacg cgcccccacc cttcgggtag  13800
ggggaaaggc cgctaaagcg gctaaaagcg ctccagcgta tttctgcggg gtttggtgtg  13860
gggtttagcg ggctttgccc gcctttcccc ctgccgcgca gcggtggggc ggtgtgtagc  13920
ctagcgcagc gaatagacca gctatccggc ctctggccgg gcatattggg caagggcagc  13980
agcgccccac aagggcgctg ataaccgcgc ctagtggatt attcttagat aatcatggat  14040
ggatttttcc aacaccccgc cagcccccgc ccctgctggg tttgcaggtt tgggggcgtg  14100
acagttattg caggggttcg tgacagttat tgcagggggg cgtgacagtt attgcagggg  14160
ttcgtgacag ttagtacggg agtgacgggc actggctggc aatgtctagc aacggcaggc  14220
atttcggctg agggtaaaag aactttccgc taagcgatag actgtatgta aacacagtat  14280
tgcaaggacg cggaacatgc ctcatgtggc ggccaggacg gccagccggg atcgggatac  14340
tggtcgttac cagagccacc gacccgagca aacccttctc tatcagatcg ttgacgagta  14400
ttacccggca ttcgctgcgc ttatggcaga gcagggaaag gaattgccgg gctatgtgca  14460
acgggaattt gaagaatttc tccaatgcgg gcggctggag catggctttc tacgggttcg  14520
ctgcgagtct tgccacgccg agcacctggt cgctttcagc tgtaagcgtc gcggtttctg  14580
```

-continued

```
cccgagctgt ggggcgcggc ggatggccga aagtgccgcc ttgctggttg atgaagtact  14640

gcctgaacaa cccatgcgtc agtgggtgtt gagcttcccg tttcagctgc gtttcctgtt  14700

tggggtcgtt tgcgggaagg ggcggaatcc tacgctaagg ctttggccag cgatattctc  14760

cggtgagatt gatgtgttcc caggggatag gagaagtcgc ttgatatcta gtatgacgtc  14820

tgtcgcacct gcttgatcgc ggcccaaggg ttggtttgcg cattcacagt tctccgcaag  14880

aattgattgg ctccaattct tggagtggtg aatccgttag cgaggtgccg ccggcttcca  14940

ttcaggtcga ggtggcccgg ctccatgcac cgcgacgcaa cgcggggagg cagacaaggt  15000

atagggcggc gcctacaatc catgccaacc cgttccatgt gctcgccgag gcggcataaa  15060

tcgccgtgac gatcagcggt ccagtgatcg aagttaggct ggtaagagcc gcgagcgatc  15120

cttgaagctg tccctgatgg tcgtcatcta cctgcctgga cagcatggcc tgcaacgcgg  15180

gcatcccgat gccgccggaa gcgagaagaa tcataatggg gaaggccatc cagcctcgcg  15240

tcgcgaacgc cagcaagacg tagcccagcg cgtcggccgc catgccggcg ataatggcct  15300

gcttctcgcc gaaacgtttg gtggcgggac cagtgacgaa ggcttgagcg agggcgtgca  15360

agattccgaa taccgcaagc gacaggccga tcatcgtcgc gctccagcga aagcggtcct  15420

cgccgaaaat gacccagagc gctgccggca cctgtcctac gagttgcatg ataaagaaga  15480

cagtcataag tgcggcgacg atagtcatgc cccgcgccca ccggaaggag ctgactgggt  15540

tgaaggctct caagggcatc ggtcgacgct ctcccttatg cgactcctgc attaggaagc  15600

agcccagtag taggttgagg ccgttgagca ccgccgccgc aaggaatggt gcatgcaagg  15660

agatggcgcc caacagtccc ccggccacgg ggcctgccac catacccacg ccgaaacaag  15720

cgctcatgag cccgaagtgg cgagcccgat cttccccatc ggtgatgtcg gcgatatagg  15780

cgccagcaac cgcacctgtg gcgccggtga tgccggccac gatgcgtccg gcgtagagga  15840

tccacaggac gggtgtggtc gccatgatcg cgtagtcgat agtggctcca agtagcgaag  15900

cgagcaggac tgggcggcgg ccaaagcggt cggacagtgc tccgagaacg ggtgcgcata  15960

gaaattgcat caacgcatat agcgctagca gcacgccata gtgactggcg atgctgtcgg  16020

aatggacgat atcccgcaag aggcccggca gtaccggcat aaccaagcct atgcctacag  16080

catccagggt gacggtgccg aggatgacga tgagcgcatt gttagatttc atacacggtg  16140

cctgactgcg ttagcaattt aactgtgata aactaccgca ttaaagctta tcgatgataa  16200

gctgtcaaac atga                                                    16214
```

<210> SEQ ID NO 9
<211> LENGTH: 427
<212> TYPE: PRT
<213> ORGANISM: Pantoea ananatis

<400> SEQUENCE: 9

```
Met Ala Asp Thr Lys Ala Lys Leu Thr Leu Asn Gly Asp Thr Ala Val
  1               5                  10                  15

Glu Leu Asp Val Leu Lys Gly Thr Leu Gly Gln Asp Val Ile Asp Ile
             20                  25                  30

Arg Thr Leu Gly Ser Lys Gly Val Phe Thr Phe Asp Pro Gly Phe Thr
         35                  40                  45

Ser Thr Ala Ser Cys Glu Ser Lys Ile Thr Phe Ile Asp Gly Asp Glu
     50                  55                  60

Gly Ile Leu Leu His Arg Gly Phe Pro Ile Asp Gln Leu Ala Thr Asp
 65                  70                  75                  80
```

-continued

```
Ser Asn Tyr Leu Glu Val Cys Tyr Ile Leu Leu Asn Gly Glu Lys Pro
                85                  90                  95

Thr Gln Glu Gln Tyr Asp Glu Phe Lys Thr Thr Val Thr Arg His Thr
            100                 105                 110

Met Ile His Glu Gln Ile Thr Arg Leu Phe His Ala Phe Arg Arg Asp
        115                 120                 125

Ser His Pro Met Ala Val Met Cys Gly Ile Thr Gly Ala Leu Ala Ala
    130                 135                 140

Phe Tyr His Asp Ser Leu Asp Val Asn Asn Pro Arg His Arg Glu Ile
145                 150                 155                 160

Ala Ala Phe Arg Leu Leu Ser Lys Met Pro Thr Met Ala Ala Met Cys
                165                 170                 175

Tyr Lys Tyr Ser Ile Gly Gln Pro Phe Val Tyr Pro Arg Asn Asp Leu
            180                 185                 190

Ser Tyr Ala Gly Asn Phe Leu Asn Met Met Phe Ser Thr Pro Cys Glu
        195                 200                 205

Pro Tyr Glu Val Asn Pro Ile Leu Glu Arg Ala Met Asp Arg Ile Leu
    210                 215                 220

Ile Leu His Ala Asp His Glu Gln Asn Ala Ser Thr Ser Thr Val Arg
225                 230                 235                 240

Thr Ala Gly Ser Ser Gly Ala Asn Pro Phe Ala Cys Ile Ala Ala Gly
                245                 250                 255

Ile Ala Ser Leu Trp Gly Pro Ala His Gly Gly Ala Asn Glu Ala Ala
            260                 265                 270

Leu Lys Met Leu Glu Glu Ile Ser Ser Val Lys His Ile Pro Glu Phe
        275                 280                 285

Phe Arg Arg Ala Lys Asp Lys Asn Asp Ser Phe Arg Leu Met Gly Phe
    290                 295                 300

Gly His Arg Val Tyr Lys Asn Tyr Asp Pro Arg Ala Thr Val Met Arg
305                 310                 315                 320

Glu Thr Cys His Glu Val Leu Lys Glu Leu Gly Thr Lys Asp Asp Leu
                325                 330                 335

Leu Glu Val Ala Met Glu Leu Glu Asn Ile Ala Leu Asn Asp Pro Tyr
            340                 345                 350

Phe Ile Glu Lys Lys Leu Tyr Pro Asn Val Asp Phe Tyr Ser Gly Ile
        355                 360                 365

Ile Leu Lys Ala Met Gly Ile Pro Ser Ser Met Phe Thr Val Ile Phe
    370                 375                 380

Ala Met Ala Arg Thr Val Gly Trp Ile Ala His Trp Ser Glu Met His
385                 390                 395                 400

Ser Asp Gly Met Lys Ile Ala Arg Pro Arg Gln Leu Tyr Thr Gly Tyr
                405                 410                 415

Glu Lys Arg Asp Phe Lys Ser Asp Ile Lys Arg
            420                 425


<210> SEQ ID NO 10
<211> LENGTH: 447
<212> TYPE: PRT
<213> ORGANISM: Pantoea ananatis

<400> SEQUENCE: 10

Met Asp Gln Thr Tyr Ser Leu Glu Ser Phe Leu Asn His Val Gln Lys
  1               5                  10                  15

Arg Asp Pro Asn Gln Thr Glu Phe Ala Gln Ala Val Arg Glu Val Met
```

-continued

```
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Ile Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Leu Pro Val Asp Ile Ala Leu Pro
305                 310                 315                 320

Cys Ala Thr Gln Asn Glu Leu Asp Val Asp Ala Ala His Gln Leu Ile
                325                 330                 335

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
        355                 360                 365

Gly Lys Ala Ala Asn Ala Gly Gly Val Ala Thr Ser Gly Leu Glu Met
    370                 375                 380

Pro Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
            420                 425                 430

Gly Phe Val Lys Val Ala Asp Ala Met Leu Ala Gln Gly Val Ile
        435                 440                 445
```

<210> SEQ ID NO 11
<211> LENGTH: 883
<212> TYPE: PRT
<213> ORGANISM: Pantoea ananatis

<400> SEQUENCE: 11

```
Met Asn Glu Gln Tyr Ser Ala Leu Arg Ser Asn Val Ser Met Leu Gly
  1               5                  10                  15

Lys Val Leu Gly Glu Thr Ile Lys Asp Ala Leu Gly Glu His Ile Leu
             20                  25                  30

Glu Arg Val Glu Thr Ile Arg Lys Leu Ser Lys Ser Ser Arg Ala Gly
         35                  40                  45

Asn Asp Ala Asn Arg Gln Glu Leu Leu Thr Thr Leu Gln Asn Leu Ser
     50                  55                  60

Asn Asp Glu Leu Leu Pro Val Ala Arg Ala Phe Ser Gln Phe Leu Asn
 65                  70                  75                  80

Leu Ala Asn Thr Ala Glu Gln Tyr His Ser Ile Ser Pro Lys Gly Glu
                 85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
        195                 200                 205

Val Glu Asn Ser Leu Trp Gln Gly Val Pro Asn Tyr Leu Arg Glu Leu
    210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
            260                 265                 270

Trp Lys Ala Thr Asp Leu Phe Leu Lys Asp Ile Gln Val Leu Val Ser
        275                 280                 285

Glu Leu Ser Met Val Glu Ala Thr Pro Glu Leu Leu Ala Leu Val Gly
    290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
            340                 345                 350

Trp Glu Pro Leu Tyr Ala Cys Tyr Gln Ser Leu Gln Ala Cys Gly Met
        355                 360                 365

Gly Ile Ile Ala Asn Gly Asp Leu Leu Asp Thr Leu Arg Arg Val Lys
```

-continued

```
    370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
            420                 425                 430

Glu Leu Asn Ser Lys Arg Pro Leu Leu Pro Arg Asn Trp Gln Pro Ser
        435                 440                 445

Ala Glu Thr Arg Glu Val Leu Asp Thr Cys Gln Val Ile Ala Glu Ala
    450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
            500                 505                 510

Asn Ala Asn Asp Val Met Thr Gln Leu Leu Asn Ile Asp Trp Tyr Arg
        515                 520                 525

Gly Leu Ile Gln Gly Lys Gln Met Val Met Ile Gly Tyr Ser Asp Ser
    530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
            580                 585                 590

His Ala Ala Leu Leu Ser Gln Pro Pro Gly Ser Leu Lys Gly Gly Leu
        595                 600                 605

Arg Val Thr Glu Gln Gly Glu Met Ile Arg Phe Lys Tyr Gly Leu Pro
    610                 615                 620

Glu Ile Thr Val Ser Ser Leu Ser Leu Tyr Thr Gly Ala Ile Leu Glu
625                 630                 635                 640

Ala Asn Leu Leu Pro Pro Pro Glu Pro Lys Glu Ser Trp Arg Arg Ile
                645                 650                 655

Met Asp Glu Leu Ser Val Ile Ser Cys Asp Val Tyr Arg Gly Tyr Val
            660                 665                 670

Arg Glu Asn Lys Asp Phe Val Pro Tyr Phe Arg Ser Ala Thr Pro Glu
        675                 680                 685

Gln Glu Leu Gly Lys Leu Pro Leu Gly Ser Arg Pro Ala Lys Arg Arg
    690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
        755                 760                 765

Met Val Phe Ala Lys Ala Asp Leu Trp Leu Ala Glu Tyr Tyr Asp Gln
    770                 775                 780

Arg Leu Val Asp Lys Ala Leu Trp Pro Leu Gly Lys Glu Leu Arg Asn
785                 790                 795                 800
```

-continued

```
Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
        835                 840                 845

Arg Ser Arg Gln Ala Glu Lys Glu Gly Gln Glu Pro Asp Pro Arg Val
    850                 855                 860

Glu Gln Ala Leu Met Val Thr Ile Ala Gly Ile Ala Ala Gly Met Arg
865                 870                 875                 880

Asn Thr Gly


<210> SEQ ID NO 12
<211> LENGTH: 6035
<212> TYPE: DNA
<213> ORGANISM: Artificial Sequence
<220> FEATURE:
<223> OTHER INFORMATION: plasmid pSTVCB
<220> FEATURE:
<221> NAME/KEY: CDS
<222> LOCATION: (2129)..(3439)

<400> SEQUENCE: 12

cgtatggcaa tgaaagacgg tgagctggtg atatgggata gtgttcaccc ttgttacacc     60

gttttccatg agcaaactga aacgttttca tcgctctgga gtgaatacca cgacgatttc    120

cggcagtttc tacacatata ttcgcaagat gtggcgtgtt acggtgaaaa cctggcctat    180

ttccctaaag ggtttattga gaatatgttt ttcgtctcag ccaatccctg ggtgagtttc    240

accagttttg atttaaacgt ggccaatatg gacaacttct tcgcccccgt tttcaccatg    300

ggcaaatatt atacgcaagg cgacaaggtg ctgatgccgc tggcgattca ggttcatcat    360

gccgtctgtg atggcttcca tgtcggcaga atgcttaatg aattacaaca gtactgcgat    420

gagtggcagg gcggggcgta attttttaa ggcagttatt ggtgccctta aacgcctggt     480

gctacgcctg aataagtgat aataagcgga tgaatggcag aaattcgaaa gcaaattcga    540

cccggtcgtc ggttcagggc agggtcgtta aatagccgct tatgtctatt gctggtttac    600

cggtttattg actaccggaa gcagtgtgac cgtgtgcttc tcaaatgcct gaggccagtt    660

tgctcaggct ctccccgtgg aggtaataat tgacgatatg atcatttatt ctgcctccca    720

gagcctgata aaaacggtta gcgcttcgtt aatacagatg taggtgttcc acagggtagc    780

cagcagcatc ctgcgatgca gatccggaac ataatggtgc agggcgcttg tttcggcgtg    840

ggtatggtgg caggccccgt ggccggggga ctgttgggcg ctgccggcac ctgtcctacg    900

agttgcatga taaagaagac agtcataagt gcggcgacga tagtcatgcc ccgcgcccac    960

cggaaggagc taccggacag cggtgcggac tgttgtaact cagaataaga aatgaggccg   1020

ctcatggcgt tccaatacgc aaaccgcctc tccccgcgcg ttggccgatt cattaatgca   1080

gctggcacga caggtttccc gactggaaag cgggcagtga gcgcaacgca attaatgtga   1140

gttagctcac tcattaggca ccccaggctt tacactttat gcttccggct cgtatgttgt   1200

gtggaattgt gagcggataa caatttcaca caggaaacag ctatgaccat gattacgcca   1260

agcttgcatg cctgcaggtc gactctagag gatccgtcga caatagcctg aatctgttct   1320

ggtcgaacct tggaaggtcc gcagccgaaa cggccgtcgc cagggatgaa ctcagagggc   1380

agggtgggga agtcggtcat gtcttcgggc aactttctgc gcttggaagt aaaagggcca   1440
```

-continued

```
gggatcgtta acgatctgac ccaacaacta taaccctgaa gctgtcagtt cctagcaccc   1500

tagattcttc acgcagtctc ccaaacgatg aaaaacgccc aaaactggcg acaccgaact   1560

attgaaaacg cgggggttag ttgaccagcc accaatttgg gggtagttca aagttttgca   1620

aagttttcaa tttctaggtt gttaatatcc cctgaggttg cgttataggg tggcgaattg   1680

catggggaaa gctactcggc acccatcctt gtcgcgtgca tcacaaactt tgctaaactg   1740

tgtaccagtc cacttattgt gggattttta atgccttaaa ggccagcatt ttcaccctct   1800

agcggggttg aatgctggcc ttgagggtgc agaactaaat agcagcacat cggcacaatt   1860

gatctgagtt ctattggcgt gaccgtggct actgattacg gtggctgtgg gtggtcggga   1920

atgatgtaac caacgtgatt gtgggggaat tggctctcac ttcggatatg gctaaaccgc   1980

atttatcggt atagcgtgtt aaccggacca gattgggaaa gaaatgtgtc gagtaacaaa   2040

aactgacatg cgcttggcgc atcccagttg gtaagaataa acgggactac ttccgtaatc   2100

cggaagagtt tttttccgaa caaat atg ttt gaa agg gat atc gtg gct act     2152
                            Met Phe Glu Arg Asp Ile Val Ala Thr
                              1               5

gat aac aac aag gct gtc ctg cac tac ccc ggt ggc gag ttc gaa atg     2200
Asp Asn Asn Lys Ala Val Leu His Tyr Pro Gly Gly Glu Phe Glu Met
 10                  15                  20                  25

gac atc atc gag gct tct gag ggt aac aac ggt gtt gtc ctg ggc aag     2248
Asp Ile Ile Glu Ala Ser Glu Gly Asn Asn Gly Val Val Leu Gly Lys
                 30                  35                  40

atg ctg tct gag act gga ctg atc act ttt gac cca ggt tat gtg agc     2296
Met Leu Ser Glu Thr Gly Leu Ile Thr Phe Asp Pro Gly Tyr Val Ser
             45                  50                  55

act ggc tcc acc gag tcg aag atc acc tac atc gat ggc gat gcg gga     2344
Thr Gly Ser Thr Glu Ser Lys Ile Thr Tyr Ile Asp Gly Asp Ala Gly
         60                  65                  70

atc ctg cgt tac cgc ggc tat gac atc gct gat ctg gct gag aat gcc     2392
Ile Leu Arg Tyr Arg Gly Tyr Asp Ile Ala Asp Leu Ala Glu Asn Ala
     75                  80                  85

acc ttc aac gag gtt tct tac cta ctt atc aac ggt gag cta cca acc     2440
Thr Phe Asn Glu Val Ser Tyr Leu Leu Ile Asn Gly Glu Leu Pro Thr
 90                  95                 100                 105

cca gat gag ctt cac aag ttt aac gac gag att cgc cac cac acc ctt     2488
Pro Asp Glu Leu His Lys Phe Asn Asp Glu Ile Arg His His Thr Leu
                110                 115                 120

ctg gac gag gac ttc aag tcc cag ttc aac gtg ttc cca cgc gac gct     2536
Leu Asp Glu Asp Phe Lys Ser Gln Phe Asn Val Phe Pro Arg Asp Ala
            125                 130                 135

cac cca atg gca acc ttg gct tcc tcg gtt aac att ttg tct acc tac     2584
His Pro Met Ala Thr Leu Ala Ser Ser Val Asn Ile Leu Ser Thr Tyr
        140                 145                 150

tac cag gat cag ctg aac cca ctc gat gag gca cag ctt gat aag gca     2632
Tyr Gln Asp Gln Leu Asn Pro Leu Asp Glu Ala Gln Leu Asp Lys Ala
    155                 160                 165

acc gtt cgc ctc atg gca aag gtt cca atg ctg gct gcg tac gca cac     2680
Thr Val Arg Leu Met Ala Lys Val Pro Met Leu Ala Ala Tyr Ala His
170                 175                 180                 185

cgc gca cgc aag ggt gct cct tac atg tac cca gac aac tcc ctc aac     2728
Arg Ala Arg Lys Gly Ala Pro Tyr Met Tyr Pro Asp Asn Ser Leu Asn
                190                 195                 200

gcg cgt gag aac ttc ctg cgc atg atg ttc ggt tac cca acc gag cca     2776
Ala Arg Glu Asn Phe Leu Arg Met Met Phe Gly Tyr Pro Thr Glu Pro
            205                 210                 215

tac gag atc gac cca atc atg gtc aag gct ctg gac aag ctg ctc atc     2824
```

-continued

```
Tyr Glu Ile Asp Pro Ile Met Val Lys Ala Leu Asp Lys Leu Leu Ile
        220                 225                 230

ctg cac gct gac cac gag cag aac tgc tcc acc tcc acc gtt cgt atg      2872
Leu His Ala Asp His Glu Gln Asn Cys Ser Thr Ser Thr Val Arg Met
    235                 240                 245

atc ggt tcc gca cag gcc aac atg ttt gtc tcc atc gct ggt ggc atc      2920
Ile Gly Ser Ala Gln Ala Asn Met Phe Val Ser Ile Ala Gly Gly Ile
250                 255                 260                 265

aac gct ctg tcc ggc cca ctg cac ggt ggc gca aac cag gct gtt ctg      2968
Asn Ala Leu Ser Gly Pro Leu His Gly Gly Ala Asn Gln Ala Val Leu
                270                 275                 280

gag atg ctc gaa gac atc aag aac aac cac ggt ggc gac gca acc gcg      3016
Glu Met Leu Glu Asp Ile Lys Asn Asn His Gly Gly Asp Ala Thr Ala
            285                 290                 295

ttc atg aac aag gtc aag aac aag gaa gac ggc gtc cgc ctc atg ggc      3064
Phe Met Asn Lys Val Lys Asn Lys Glu Asp Gly Val Arg Leu Met Gly
        300                 305                 310

ttc gga cac cgc gtt tac aag aac tac gat cca cgt gca gca atc gtc      3112
Phe Gly His Arg Val Tyr Lys Asn Tyr Asp Pro Arg Ala Ala Ile Val
    315                 320                 325

aag gag acc gca cac gag atc ctc gag cac ctc ggt ggc gac gat ctt      3160
Lys Glu Thr Ala His Glu Ile Leu Glu His Leu Gly Gly Asp Asp Leu
330                 335                 340                 345

ctg gat ctg gca atc aag ctg gaa gaa att gca ctg gct gat gat tac      3208
Leu Asp Leu Ala Ile Lys Leu Glu Glu Ile Ala Leu Ala Asp Asp Tyr
                350                 355                 360

ttc atc tcc cgc aag ctc tac ccg aac gta gac ttc tac acc ggc ctg      3256
Phe Ile Ser Arg Lys Leu Tyr Pro Asn Val Asp Phe Tyr Thr Gly Leu
            365                 370                 375

atc tac cgc gca atg ggc ttc cca act gac ttc ttc acc gta ttg ttc      3304
Ile Tyr Arg Ala Met Gly Phe Pro Thr Asp Phe Phe Thr Val Leu Phe
        380                 385                 390

gca atc ggt cgt ctg cca gga tgg atc gct cac tac cgc gag cag ctc      3352
Ala Ile Gly Arg Leu Pro Gly Trp Ile Ala His Tyr Arg Glu Gln Leu
    395                 400                 405

ggt gca gca ggc aac aag atc aac cgc cca cgc cag gtc tac acc ggc      3400
Gly Ala Ala Gly Asn Lys Ile Asn Arg Pro Arg Gln Val Tyr Thr Gly
410                 415                 420                 425

aag gaa tcc cgc aag ttg gtt cct cgc gag gag cgc taaatttagc           3446
Lys Glu Ser Arg Lys Leu Val Pro Arg Glu Glu Arg
                430                 435

ggatgattct cgttcaactt cggccgaagc cacttcgtct gtcataatga cagggatggt   3506

ttcggccgtt tttgcatgaa accaaaaaat acgattttca aggagcatgt acagcacatg   3566

gaaaagccac agattgagct accggtcggt ccagcaccgg aagatctcgt aatctctgac   3626

atcatcgttg gcgaaggcgc agaagcccgc ccaggcggag aagttgaggt ccactatgtg   3686

ggcgttgacc ttgaaaccgg cgaggagttt gactcttcct gggatcgtgg acagaccagc   3746

cagttcccac tcaacggcct cattgcaggt tggcaagaag gaattccagg catgaaggtc   3806

ggcggacgtc gtcagctgac cattccgcca gaggctgctt acggccctga gggttccggc   3866

cacccactgt ctggccgtac cctggtgttc atcatcgatt tgatcagcgc ataattttct   3926

ttactgcgct aaacgctcaa atcgtgtgaa gcgactgtcg cgtcctgccc tctccggatt   3986

gttatccaat tcggagaggg cgttgctgat tgtgccgaga atttcttcaa caaagtgctc   4046

ggtttcggcg acgatcccgt cgataagccc ttggcttaaa agtgcgtgcg cctgcacgcc   4106

ttgtcgctct atgatttccg cggcgtggtt ggtgtcgcgg aagaggatgg ccgaggcgcc   4166
```

-continued

```
ctctggaggc aatgcggaca gccacgcgtt ttcggccgcg tagaccagat cggcgggcag   4226

catggccagc gcgccaccgc caacgccctg accaataatg accgaaacgg tggggagggg   4286

agcgtcgata agcttgcatg cctgcaggtc gactctagag gatccccggg taccgagctc   4346

gaattcactg gccgtcgttt tacaacgtcg tgactgggaa aaccctggcg ttacccaact   4406

taatcgcctt gcagcacatc cccctttcgc cagctggcgt aatagcgaag aggcccgcac   4466

cgatcgccct tcccaacagt tgcgcagcct gaatggcgaa tgagcttatc gatgataagc   4526

tgtcaaacat gagaattaca acttatatcg tatggggctg acttcaggtg ctacatttga   4586

agagataaat tgcactgaaa tctagaaata ttttatctga ttaataagat gatcttcttg   4646

agatcgtttt ggtctgcgcg taatctcttg ctctgaaaac gaaaaaaccg ccttgcaggg   4706

cggtttttcg aaggttctct gagctaccaa ctctttgaac cgaggtaact ggcttggagg   4766

agcgcagtca ccaaaacttg tcctttcagt ttagccttaa ccggcgcatg acttcaagac   4826

taactcctct aaatcaatta ccagtggctg ctgccagtgg tgcttttgca tgtctttccg   4886

ggttggactc aagacgatag ttaccggata aggcgcagcg gtcggactga acggggggtt   4946

cgtgcataca gtccagcttg gagcgaactg cctacccgga actgagtgtc aggcgtggaa   5006

tgagacaaac gcggccataa cagcggaatg acaccggtaa accgaaaggc aggaacagga   5066

gagcgcacga gggagccgcc aggggaaacg cctggtatct ttatagtcct gtcgggtttc   5126

gccaccactg atttgagcgt cagatttcgt gatgcttgtc aggggggcgg agcctatgga   5186

aaaacggctt tgccgcggcc ctctcacttc cctgttaagt atcttcctgg catcttccag   5246

gaaatctccg ccccgttcgt aagccatttc cgctcgccgc agtcgaacga ccgagcgtag   5306

cgagtcagtg agcgaggaag cggaatatat cctgtatcac atattctgct gacgcaccgg   5366

tgcagccttt tttctcctgc cacatgaagc acttcactga caccctcatc agtgccaaca   5426

tagtaagcca gtatacactc cgctagcgct gatgtccggc ggtgcttttg ccgttacgca   5486

ccaccccgtc agtagctgaa caggagggac agctgataga aacagaagcc actggagcac   5546

ctcaaaaaca ccatcataca ctaaatcagt aagttggcag catcacccga cgcactttgc   5606

gccgaataaa tacctgtgac ggaagatcac ttcgcagaat aaataaatcc tggtgtccct   5666

gttgataccg ggaagccctg ggccaacttt tggcgaaaat gagacgttga tcggcacgta   5726

agaggttcca actttcacca taatgaaata agatcactac cgggcgtatt ttttgagtta   5786

tcgagatttt caggagctaa ggaagctaaa atggagaaaa aaatcactgg atataccacc   5846

gttgatatat cccaatggca tcgtaaagaa cattttgagg catttcagtc agttgctcaa   5906

tgtacctata accagaccgt tcagctggat attacggcct ttttaaagac cgtaaagaaa   5966

aataagcaca agttttatcc ggcctttatt cacattcttg cccgcctgat gaatgctcat   6026

ccggaattt                                                          6035
```

<210> SEQ ID NO 13
<211> LENGTH: 437
<212> TYPE: PRT
<213> ORGANISM: Brevibacterium lactofermentum

<400> SEQUENCE: 13

```
Met Phe Glu Arg Asp Ile Val Ala Thr Asp Asn Asn Lys Ala Val Leu
  1               5                  10                  15

His Tyr Pro Gly Gly Glu Phe Glu Met Asp Ile Ile Glu Ala Ser Glu
             20                  25                  30

Gly Asn Asn Gly Val Val Leu Gly Lys Met Leu Ser Glu Thr Gly Leu
```

-continued

```
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Asn Asn His Gly Gly Asp Ala Thr Ala Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Lys Glu Ser Arg Lys Leu Val
            420                 425                 430

Pro Arg Glu Glu Arg
        435
```

PROCESS FOR PRODUCING L-GLUTAMIC ACID

The present invention claims priority under 35 U.S.C. §119 to Japanese Patent Application No. 2003-165545, filed Jun. 10, 2003, and is a continuation under 35 U.S.C. §120 of PCT/JP2004/008140, filed Jun. 10, 2004, the entirety of both of which is incorporated by reference.

BACKGROUND OF THE INVENTION

1. Field of the Invention

The present invention relates to a method for producing L-glutamic acid by fermentation. L-glutamic acid is widely used as a raw material in the production of seasonings and so forth.

2. Description of the Related Art

L-glutamic acid is mainly produced by fermentation using an L-glutamic acid-producing bacterium of the so-called coryneform bacterium belonging to the genus *Brevibacterium, Corynebacterium* or *Microbacterium* or mutant strains thereof. Moreover, methods utilizing a microorganism belonging to the genus *Bacillus, Streptomyces, Penicillium, Pseudomonas, Arthrobacter, Serratia, Candida*, or *Aerobacter aerogenes* (currently *Enterobacter aerogenes*), a mutant strain of *Escherichia coli*, or the like are known. Furthermore, also known are methods of producing L-glutamic acid using a microorganism belonging to the genus *Klebsiella, Erwinia*, or *Pantoea* (U.S. Pat. No. 6,197,559), and methods of producing L-glutamic acid using an *Enterobacter* bacterium (U.S. Pat. No. 6,331,419).

Furthermore, various techniques for improving L-glutamic acid-producing ability by enhancing activities of L-glutamic acid biosynthetic enzymes through the use of recombinant DNA techniques have been disclosed. For example, it was reported that the introduction of a gene encoding citrate synthase derived from *Escherichia coli* or *Corynebacterium glutamicum* was-effective for enhancing L-glutamic acid-producing ability in bacterium belonging to the genus *Corynebacterium* or *Brevibacterium* (Japanese Patent Publication (JP 7-121228 B). In addition, JP 61-268185 A discloses a cell harboring recombinant DNA containing a glutamate dehydrogenase gene derived from *Corynebacterium* bacteria. Furthermore, JP 63-214189 A discloses a technique for increasing L-glutamic acid-producing ability by amplifying genes encoding glutamate dehydrogenase, isocitrate dehydrogenase, aconitate hydratase, and a citrate synthase.

L-glutamic acid production has been considerably increased by the aforementioned breeding of microorganisms or improving production methods. However, in order to respond to increased demand in the future, the development of methods which provide more efficient production of L-glutamic acid at a lower cost are still necessary, and therefore, still represent a need in the art.

Methods for L-glutamic acid fermentation while precipitating L-glutamic acid, which accumulates in culture broth, have been developed (EP 1078989 A). Because the usual L-glutamic acid-producing bacteria cannot grow under acidic conditions, L-glutamic acid fermentation was conventionally performed under neutral conditions. Contrary to such conventional techniques, microorganisms which could produce L-glutamic acid under acidic conditions were screened, and it has been reported that L-glutamic acid can be produced and accumulated in the medium while precipitating the L-glutamic acid by culturing the obtained microorganism (*Enterobacter agglomerans*) in a liquid medium in which the pH is controlled so that L-glutamic acid is precipitated.

Furthermore, methods are known for producing L-glutamic acid by culturing such an L-glutamic acid-producing bacterium that can grow under acidic conditions as described above in a medium having a total content of organic acids that inhibit growth of the bacterium in an amount that does not inhibit the growth of the bacterium (European Patent Application Laid-open No. 1233070) and for producing L-glutamic acid by culturing such a bacterium as described above at a first pH optimal for growth of the microorganism and then culturing the bacterium at a second pH optimal for L-glutamic acid production by the microorganism and lower than the first pH (European Patent Application Laid-open No. 1233068). Furthermore, a method is known for producing and accumulating L-glutamic acid in a medium while precipitating the L-glutamic acid in the medium, wherein crystals of L-glutamic acid are made to exist in the medium while L-glutamic acid concentration in the medium is lower than the concentration at which natural crystallization of L-glutamic acid occurs (European Patent Application Laid-open No. 1233069).

SUMMARY OF THE INVENTION

An object of the present invention is to provide a method for more efficiently producing L-glutamic acid compared with prior art techniques by using a bacterium having an ability to produce L-glutamic acid such as a bacterium belonging to the genus *Pantoea.*

The inventors of the present invention found that if a high L-glutamic acid-producing ability was imparted to a bacterium belonging to the genus *Pantoea*, acetoin and 2,3-butanediol are also produced together with L-glutamic acid. Furthermore, they considered that if it became possible to suppress the production of these by-products, the yield of L-glutamic acid per unit amount of the main raw material (sugar) would be improved. Thus, the inventors of present invention conducted various research and, as a result, found that if pantothenic acid was added to a medium, the by-production of acetoin and 2,3-butanediol was reduced, and as a result, the fermentation yield of L-glutamic acid was improved. Thus, they accomplished the present invention.

That is, the objects of the present invention are as follows. It is an object of the present invention to provide a method for producing L-glutamic acid comprising culturing a microorganism belonging to the genus *Pantoea* in a medium which contains pantothenic acid, wherein the pH of the medium is controlled so to induce precipitation of L-glutamic acid, and collecting said L-glutamic acid from said medium.

It is a further object of the invention to provide the method as described above, wherein said microorganism is able to metabolize a carbon source in a second medium which contains L-glutamic acid at a saturation concentration and has an ability to cause accumulation of L-glutamic acid in said second medium, wherein said second medium is at a second pH.

It is a further object of the invention to provide the method as described above, wherein the microorganism is *Pantoea ananatis.*

It is a further object of the invention to provide the method as described above, wherein said pantothenic acid is a pantothenic acid salt, and the concentration of said salt is at least 1 mg/L.

DETAILED DESCRIPTION OF THE PREFERRED EMBODIMENTS

Figure 1:
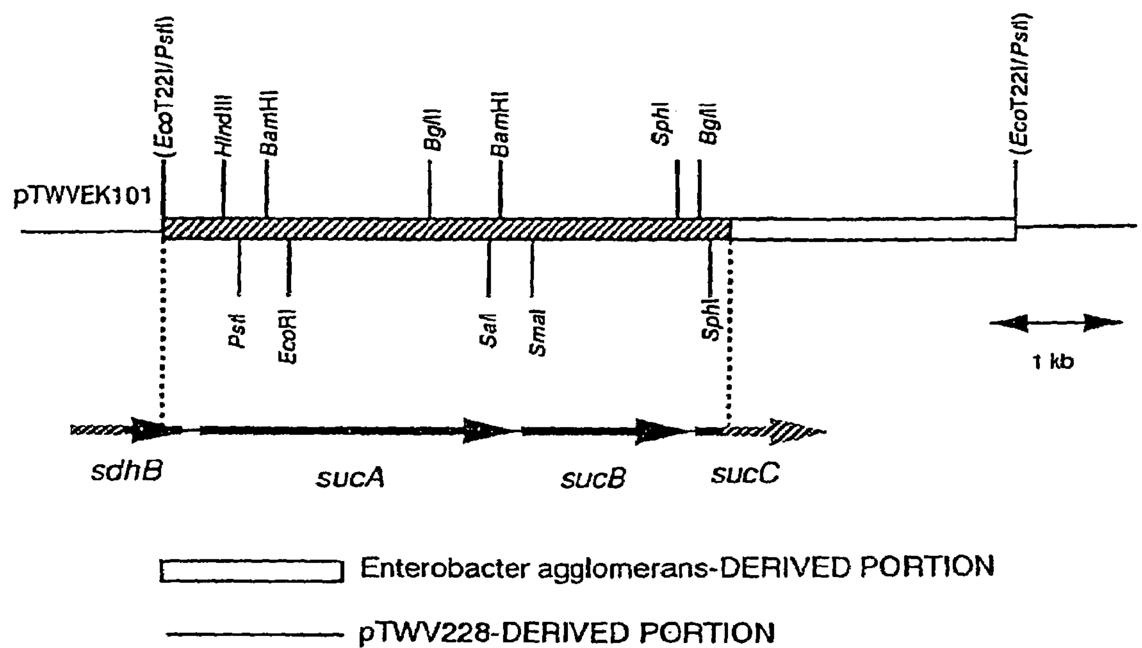
FIG. 1 shows a restriction map of a DNA fragment of pTWVEK101 derived from *Pantoea ananatis.*

Hereinafter, the present invention will be explained in detail.

The present invention provides a method for producing L-glutamic acid by fermentation by culturing a microorganism in a medium which contains pantothenic acid, wherein the pH of the medium is controlled so to induce precipitation of L-glutamic acid, and wherein said microorganism is able to metabolize a carbon source at a second pH in a second medium which contains L-glutamic acid at a saturation concentration, and wherein said microorganism has an ability to cause accumulation of L-glutamic acid in said second medium at said second pH, and wherein said L-glutamic acid accumulates in an amount exceeding the amount corresponding to the saturation concentration of L-glutamic acid (henceforth also referred to as an "L-glutamic acid-accumulating microorganism").

The above L-glutamic acid-accumulating microorganism can be obtained, for example, as follows. A sample containing microorganisms is inoculated into a liquid medium containing 1) L-glutamic acid at a saturation concentration and 2) a carbon source at a specific pH.A strain that is able to metabolize the carbon source is then selected. Although the specific pH is not particularly limited, it is usually about 5.0 or less, preferably about 4.5 or less, further preferably about 4.3 or less. The L-glutamic acid-accumulating microorganism is used for production of L-glutamic acid by fermentation with accompanying precipitation of the L-glutamic acid. If the pH is too high, it becomes difficult for the microorganism to produce L-glutamic acid in an amount sufficient for precipitation. Therefore, the pH is preferably in the aforementioned range.

If the pH of an aqueous solution containing L-glutamic acid is lowered, the solubility of L-glutamic acid significantly falls when the pH is about equal to the pKa of the γ-carboxyl group, or about 4.25 at 25° C. The solubility is the lowest at the isoelectric point (pH 3.2), and the amount of L-glutamic acid which exceeds the saturation concentration precipitates. While it depends on the composition of the medium, L-glutamic acid is dissolved in an amount of 10-20 g/L at pH 3.2, 30-40 g/L at pH 4.0 and 50-60 g/L at pH 4.7, at about 30° C. Usually the pH does not need to be 3.0 or lower, because the L-glutamic acid precipitating effect reaches its upper limit when the pH falls below a certain value. However, the pH may be 3.0 or less.

In addition, the expression that a microorganism "can metabolize a carbon source" or "is able to metabolize a carbon source" means that the microorganism can proliferate or can consume a carbon source even though it cannot proliferate, that is, it indicates that the microorganism catabolizes a carbon source such as sugars or organic acids. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can metabolize the carbon source in the medium. Furthermore, for example, if a microorganism consumes a carbon source even though the microorganism does not proliferate, when it is cultured in a synthetic liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can metabolize the carbon source in the medium.

The microorganism that can metabolize a carbon source includes a microorganism that can grow in the aforementioned liquid medium. The expression that a microorganism "can grow" means that it can proliferate, or it can produce L-glutamic acid even though it cannot proliferate. Specifically, for example, if a microorganism proliferates when it is cultured in a liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can grow in the medium. Furthermore, for example, if a microorganism increases the amount of L-glutamic acid in a synthetic liquid medium even though the microorganism does not proliferate, when the microorganism is cultured in the synthetic liquid medium containing L-glutamic acid at a saturation concentration at pH 5.0 to 4.0, preferably pH 4.5 to 4.0, more preferably pH 4.3 to 4.0, most preferably about pH 4.0, at an appropriate temperature, for example, 28° C., 37° C. or 50° C., for 2 to 4 days, then this is a microorganism that can grow in the medium.

The selection of a microorganism as described above may be repeated two or more times under the same conditions, or by changing the pH or the concentration of L-glutamic acid. Selection at an early stage can be performed in a medium containing L-glutamic acid at a concentration lower than the saturation concentration, and subsequent selection can be performed in a medium containing L-glutamic acid at the saturation concentration. Furthermore, strains with favorable properties, such as a superior proliferation rate, may be selected.

The L-glutamic acid-accumulating microorganism has an ability to cause accumulation of an amount of L-glutamic acid which exceeds the saturation concentration of L-glutamic acid in a liquid medium, in addition to the properties described above. The pH of the aforementioned liquid medium is preferably the same as or close to that of the medium used for screening a microorganism having the aforementioned properties. Usually, a microorganism becomes more sensitive to L-glutamic acid at a high concentration as the pH falls. Therefore, it is preferred that the pH is not low in view of resistance to L-glutamic acid, but a low pH is preferred for production of L-glutamic acid with accompanying precipitation. To satisfy these conditions, the pH can be in the range of 3 to 5, preferably 4 to 5, more preferably 4 to 4.7, further preferably 4 to 4.5, particularly preferably 4.0 to 4.3.

Examples of the L-glutamic acid-accumulating microorganism or breeding materials thereof include, but are not limited to, microorganisms belonging to the genus *Pantoea, Enterobacter, Klebsiella, Serratia, Erwinia, Escherichia, Corynebacterium, Brevibacterium, Alicyclobacillus, Bacillus, Saccharomyces*, or the like. Of these, microorganisms belonging to the genus *Pantoea* are preferred. Hereinafter, the microorganism of the present invention will be explained mainly for microorganisms belonging to the genus *Pantoea*. However, the microorganism is not limited to those belonging to the genus *Pantoea*, and those belonging to other genera can be similarly used.

An example of a microorganism belonging to the *Pantoea* includes, but is not limited to, *Pantoea ananatis*, preferably *Pantoea ananatis* AJ13355. This strain was isolated from soil in Iwata-shi, Shizuoka, Japan, and can proliferate in a medium containing L-glutamic acid and a carbon source at low pH.

The *Pantoea ananatis* AJ13355 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary) on Feb. 19, 1998 and received an accession number of FERM P-16644. It was then converted to an international deposit under the provisions of Budapest Treaty on Jan. 11, 1999 and received an accession number of FERM BP-6614.

The above strain was identified as *Enterobacter agglomerans* when it was isolated and deposited as the *Enterobacter agglomerans* AJ13355 strain. However, it was recently re-classified as *Pantoea ananatis* on the basis of nucleotide sequencing of 16S rRNA and so forth (see the examples section).

Although the strains AJ13356 and AJ13601 that were derived from AJ13355 strain were also deposited at the aforementioned depository as *Enterobacter agglomerans*, they are described as *Pantoea ananatis* in this specification.

The L-glutamic acid-accumulating microorganism may originally have L-glutamic acid-producing ability, or may have L-glutamic acid-producing ability imparted or increased by breeding through mutagenesis, recombinant DNA techniques, or the like.

The L-glutamic acid-producing ability can be imparted or increased by, for example, increasing an activity of an enzyme that catalyzes a biosynthetic reaction of L-glutamic acid. The L-glutamic acid-producing ability can also be increased by decreasing or eliminating activity of an enzyme that catalyzes a reaction which branches off from the biosynthetic pathway of L-glutamic acid, and generates a compound other than L-glutamic acid.

Examples of the enzyme that catalyzes the biosynthetic reaction of L-glutamic acid include, but are not limited to, glutamate dehydrogenase (hereinafter, also referred to as "GDH"), glutamine synthetase, glutamate synthase, isocitrate dehydrogenase, aconitate hydratase, citrate synthase (hereafter, also referred to as "CS"), phosphoenolpyruvate carboxylase (hereinafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth. Of these enzymes, one or any combination of CS, PEPC, and GDH are preferred. Furthermore, it is preferred that the activities of all the three of the enzymes CS, PEPC, and GDH, are enhanced in the L-glutamic acid-accumulating microorganism. In particular, CS from *Brevibacterium lactofermentum* is preferred, because it is not subject to inhibition by α-ketoglutaric acid, L-glutamic acid, and NADH.

In order to enhance the activity of CS, PEPC or GDH, for example, a gene encoding CS, PEPC or GDH can be cloned on an appropriate plasmid and transformed into a host microorganism. The copy number of the gene encoding CS, PEPC, or GDH (hereinafter, abbreviated as "gltA gene", "ppc gene", and "gdhA gene", respectively) in the transformant can be increased, resulting in an increase in the activity of CS, PEPC, or GDH.

The cloned gltA, ppc, and gdhA genes are introduced into the aforementioned starting parent strain solely or randomly in combination. When two or three kinds of the genes are introduced, they may be cloned on one plasmid and introduced into the host, or separately cloned onto two or three different plasmids that can coexist, and then introduced into the host.

Two or more genes encoding the same enzyme, but derived from different microorganisms, may be introduced into the same host.

The plasmids described above are not particularly limited so long as they are autonomously replicable in a microorganism belonging to, for example, the genus *Pantoea* or the like. Examples of these plasmids include pUC19, pUC18, pBR322, pHSG299, pHSG298, pHSG399, pHSG398, RSF1010, pMW119, pMW118, pMW219, pMW218, pACYC177, pACYC 184, and so forth. Vectors of phage DNA can also be used for introducing the aforementioned genes.

Transformation can be performed by, for example, the method of D. M. Morrison (Methods in Enzymology, 68, 326 (1979)), wherein permeability of recipient bacterium cells is increased by treating the cells with calcium chloride (Mandel M. and Higa A., J. Mol. Biol., 53, 159 (1970)), electroporation (Miller J. H., "A Short Course in Bacterial Genetics", Cold Spring Harbor Laboratory Press, U.S.A., 1992), or the like.

The activity of CS, PEPC or GDH can also be increased by allowing multiple copies of the gltA gene, the ppc gene, or the gdhA gene to be present on chromosomal DNA of the aforementioned starting parent strain. Multiple copies of the gltA gene, the ppc gene, or the gdhA gene may be introduced into the chromosomal DNA by homologous recombination. In order to introduce multiple copies of these genes into the chromosomal DNA of a bacterium belonging to the genus *Pantoea*, sequences can be used which are present on the chromosomal DNA in multiple copy number, such as a repetitive DNA and inverted repeats present at the end of a transposable element. Alternatively, multiple copies of the gltA gene, the ppc gene, or the gdhA gene can be introduced into the chromosomal DNA by incorporating them into a transposon and transferring it. As a result, the copy number of gltA gene, the ppc gene, or the gdhA gene in a transformant strain is increased, and thus the activity of CS, PEPC, or GDH is increased.

As organisms used as a source of the gltA gene, the ppc gene, or the gdhA gene of which copy number is to be increased, any organism can be used so long as it has activity of CS, PEPC, or GDH. Examples of the organism preferably include, but are not limited to, bacteria belonging to the genus *Pantoea, Enterobacter, Klebsiella, Erwinia, Serratia, Escherichia, Corynebacterium, Brevibacterium*, or *Bacillus*.

Specifically, *Escherichia coli, Brevibacterium lactofermentum* and so forth are encompassed by the present invention. The gltA gene, the ppc gene, and the gdhA gene can be obtained from chromosomal DNA of the microorganisms described above.

The gltA gene, the ppc gene, and the gdhA gene can be obtained using a mutant strain which is deficient in the activity of CS, PEPC, or GDH so that a DNA fragment is isolated that supplements its auxotrophy from the chromosomal DNA of the aforementioned microorganism. Furthermore, since the nucleotide sequences of these genes from bacteria belonging to the genera *Escherichia* and *Corynebacterium* are known (Biochemistry, 22, pp. 5243-5249, (1983); J. Biochem., 95, pp. 909-916, (1984); Gene, 27, pp. 193-199, (1984); Microbiology, 140, pp. 1817-1828, (1994); Mol. Gen. Genet., 218, pp. 330-339, (1989); Molecular Microbiology, 6, pp. 317-326, (1992)), they can also be obtained by PCR utilizing primers which have been synthesized based on each nucleotide sequence and using the chromosomal DNA as a template. It is known that, in enterobacteria such as bacteria belonging to the genus *Enterobacter* or *Klebsiella*, introduction of a gltA gene from a coryneform bacterium is more effective for enhancing the L-glutamic acid-producing ability when compared with that of a gltA gene from a bacterium of the same species (European Patent Application Laid-open No. 0999282). The strains of *Pantoea ananatis* described herein are described as *Enterobacter agglomerans*.

The activity of CS, PEPC, or GDH can also be increased by enhancing the expression of the gltA gene, the ppc gene, or the gdhA gene, besides the aforementioned amplification of the genes. For example, the expression can be enhanced by replacing a promoter for the gltA gene, the ppc gene, or the gdhA gene with a stronger promoter. For example, lac promoter, trp promoter, trc promoter, tac promoter, $P_R$ promoter and $P_L$ promoter of the lamda phage, and so forth are known as strong promoters. The gltA gene, the ppc gene and the gdhA gene which have had their respective promoters replaced are then cloned into a plasmid and introduced into the host microorganism, or introduced into the chromosomal DNA of the host microorganism using repetitive DNA, inverted repeat, transposon, or the like.

The activity of CS, PEPC, or GDH can also be increased by replacing the promoter of the gltA gene, the ppc gene, or the gdhA gene on the chromosome with a stronger promoter (see WO87/03006 and Japanese Patent Application Laid-open No. 61-268183), or inserting a strong promoter upstream of the gene coding sequence (see Gene, 29, pp. 231-241 (1984)).

Specifically, homologous recombination can be performed between the gltA gene, the ppc gene, or the gdhA gene for which the promoter is replaced with a stronger one or DNA containing a part thereof, and the corresponding gene on the chromosome.

Examples of the enzyme that catalyzes the reaction which branches off from the biosynthetic pathway of the L-glutamic acid and generates a compound other than L-glutamic acid include α-ketoglutarate dehydrogenase (hereinafter, also referred to as "αKGDH"), isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline dehydrogenase, and so forth. Of these enzymes, αKGDH is preferred.

In order to decrease or eliminate the activities of the aforementioned enzymes in a microorganism belonging to the genus *Pantoea* or the like, mutations for decreasing or eliminating the intracellular activity of the enzymes can be introduced into the genes of the aforementioned enzymes by a usual mutagenesis treatment method or a genetic engineering method.

Examples of a mutagenesis treatment method include, for example, methods utilizing irradiation with X-rays or ultraviolet rays, methods utilizing treatment with a mutagenesis agent such as N-methyl-N'-nitro-N-nitrosoguanidine, and so forth. The mutation may be introduced into the coding region for the enzyme or a region which regulates expression, such as a promoter.

Examples of the genetic engineering methods include, for example, methods utilizing gene recombination, transduction, cell fusion, and so forth. For example, a drug resistance gene is inserted into a cloned target gene to prepare a gene that has lost its function (defective gene). Subsequently, this defective gene is introduced into a host microorganism, and the target gene on the chromosome is replaced with the aforementioned defective gene by utilizing homologous recombination (gene disruption).

The decrease of intracellular activity of the target enzyme in a cell and the degree of the decrease can be confirmed by measuring the enzyme activity of a cell extract or a purified fraction thereof obtained from a candidate strain and comparing it with that of a wild-type strain. For example, the αKGDH activity can be measured by the method of Reed et al. (Reed L. J. and Mukherjee B. B., Methods in Enzymology, 13, pp. 55-61 (1969)).

Depending on the target enzyme, a target mutant strain can be selected based on the phenotype of the mutant strain. For example, a mutant strain wherein the αKGDH activity is eliminated or decreased cannot proliferate or shows a markedly reduced proliferation rate in a minimal medium containing glucose or a minimal medium containing acetic acid or L-glutamic acid as the sole carbon source under aerobic culture conditions. However, normal proliferation occurs even under the same conditions by adding succinic acid or lysine, methionine, and diaminopimelic acid to a minimal medium containing glucose. By utilizing these phenomena as indicators, a mutant strain with decreased αKGDH activity or which is deficient in the activity can be selected.

A method for preparing an αKGDH gene-deficient strain of *Brevibacterium lactofermentum* by utilizing homologous recombination is described in detail in WO95/34672. Similar methods can be applied to other microorganisms.

Furthermore, techniques such as the cloning of genes and digestion and ligation of DNA, transformation, and so forth are described in detail in Molecular Cloning, 2nd Edition, Cold Spring Harbor Press (1989), and so forth.

A specific example of a mutant strain deficient in αKGDH activity or with decreased αKGDH activity obtained as described above includes *Pantoea ananatis* AJ13356. *Pantoea ananatis* AJ13356 was deposited at the National Institute of Bioscience and Human-Technology, Agency of Industrial Science and Technology, Ministry of International Trade and Industry (currently, National Institute of Advanced Industrial Science and Technology, International Patent Organism Depositary) on Feb. 19, 1998 and received an accession number of FERM P-16645. It was then converted to an international deposit under the provisions of Budapest Treaty on Jan. 11, 1999 and received an accession number of FERM BP-6615. The *Pantoea ananatis* AJ 13356 is deficient in αKGDH activity as a result of disruption of the αKGDH-E1 subunit gene (sucA).

When *Pantoea ananatis*, which is an example of the microorganism used in the present invention, is cultured in a medium containing a saccharide, mucus is extracellularly secreted, occasionally resulting in low operation efficiency. Therefore, when *Pantoea ananatis* which secretes mucus is used, it is preferable to use a mutant strain that secretes less mucus as compared with a wild-type strain. Examples of mutagenesis treatment include, for example, methods utilizing irradiation with X-ray or ultraviolet ray, methods utilizing treatment with a mutagenesis agent such as N-methyl-N'-nitro-N-nitrosoguanidine, and so forth. A mutant strain with decreased secretion of mucus can be selected by inoculating mutagenized bacterial cells in a medium containing a saccharide, for example, an LB medium plate containing 5 g/L of glucose, culturing them while tilting the plate about 45 degrees and selecting a colony that does not show a flow of mucus.

In the present invention, the impartation or enhancement of L-glutamic acid-producing ability and the impartation of other desirable properties such as reducing mucus secretion as described above can be carried out in any order.

The nucleotide sequence of the sucA gene of *Pantoea ananatis* as a gene used for the breeding of such L-glutamic acid-producing bacteria as described above and the amino acid sequence of the αKGDH-E1 subunit encoded by the gene are shown SEQ ID NO: 1 and SEQ ID NO: 3.

Furthermore, the nucleotide sequence of the plasmid RSFCPG containing the gltA gene, gdhA gene, and ppc gene derived from *Escherichia coli* (see Reference Example 1) is shown in SEQ ID NO: 8. In SEQ ID NO: 8, the coding regions of the gltA gene, gdhA gene, and ppc gene are shown at nucleotide numbers 1770 to 487 (encoded by the complementary strand), 2598 to 3941, and 7869 to 5218 (encoded by the complementary strand), respectively. The amino acid sequences of CS, GDH, and PEPC encoded by these genes are shown in SEQ ID NOS: 9, 10, and 11, respectively. Furthermore, the nucleotide sequence of plasmid pSTVCB containing the gltA gene derived from *Brevibacterium lactofermentum* (see Reference Example 1) and the amino acid sequence of CS encoded by this gene are shown in SEQ ID NO: 12 and SEQ ID NO: 13, respectively.

CS, GDH, and PEPC may include, besides the wild-type sequences, sequences which have substitution, deletion, insertion, addition, or inversion of one or several amino acid residues that do not substantially degrade the activities of the enzymes. Although the number of "several" amino acid residues referred to herein differs depending on positions in the three-dimensional structures of the proteins or types of amino acid residues, it may be specifically between 2 to 30, preferably between 2 to 20, more preferably between 2 to 10. Therefore, changes to CS, GDH, or PEPC such as those described above are typically conservative changes so as to maintain the activity of CS, GDH, or PEPC. Substitution changes include those in which at least one residue in the amino acid sequence has been removed and a different residue inserted in its place. Examples of amino acids which may be substituted for an original amino acid in a CS, GDH, or PEPC protein and which are regarded as conservative substitutions include: Ala substituted with ser or thr; arg substituted with gln, his, or lys; asn substituted with glu, gln, lys, his, or asp; asp substituted with asn, glu, or gln; cys substituted with ser or ala; gln substituted with asn, glu, lys, his, asp, or arg; glu substituted with asn, gln, lys, or asp; gly substituted with pro; his substituted with asn, lys, gln, arg, or tyr; ile substituted with leu, met, val, or phe; leu substituted with ile, met, val, or phe; lys substituted with asn, glu, gln, his, or arg; met substituted with ile, leu, val, or phe; phe substituted with trp, tyr, met, ile, or leu; ser substituted with thr or ala; thr substituted with ser or ala; trp substituted with phe or tyr; tyr substituted with his, phe, or trp; and val substituted with met, ile, or leu.

Examples of DNA coding for substantially the same protein or peptide as CS, GDH, or PEPC include DNA hybridizable with an open reading frame (ORF) of the nucleotide sequence shown in SEQ ID NO: 12 or SEQ ID NO: 8, or a probe that can be prepared from the nucleotide sequence under stringent conditions and encodes a protein having the activity of CS, GDH, or PEPC. The "stringent conditions" referred to herein include conditions under which so-called specific hybrid is formed, and non-specific hybrid is not formed. It is difficult to clearly express this condition by using any numerical value. However, for example, stringent conditions may include conditions under which DNAs having high homology, for example, DNAs having homology of not less than 50%, preferably not less than 70%, more preferably not less than 90%, most preferably not less than 95% hybridize with each other, but DNAs having homology lower than the above do not hybridize with each other. Alternatively, stringent conditions include conditions whereby DNAs hybridize with each other at a salt concentration typically used during washing in Southern hybridization, i.e., 1×SSC, 0.1% SDS, preferably 0.1×SSC, 0.1% SDS, at 60° C.

The ORF of the nucleotide sequence of SEQ ID NO: 12 or SEQ ID NO: 8 or a partial sequence thereof can also be used as the probe. Such a probe can be prepared by PCR using oligonucleotides based on the nucleotide sequence of SEQ ID NO: 8 or 12 as primers and a DNA fragment containing the nucleotide sequence of SEQ ID NO: 8 or 12 or a partial nucleotide sequence thereof as a template. When a DNA fragment having a length of about 300 bp is used as the probe, the washing conditions for the hybridization can be, for example, 2×SSC and 0.1% SDS at 50° C.

It is sufficient that the deletion-type sucA gene used for gene disruption has homology to such a degree that it causes homologous recombination with the sucA gene on a chromosomal DNA of an objective microorganism. Such homology is preferably not less than 85%, more preferably not less than 90%, particularly preferably not less than 95%. Moreover, DNAs hybridizable under stringent conditions may cause homologous recombination.

Specific examples of such a strain obtained as described above include the AJ13601 strain derived from the aforementioned *Pantoea ananatis* AJ13355 strain. This strain was obtained by selecting a low mucus-producing strain from the AJ13355 strain, disrupting the αKGDH gene, introducting the gltA, ppc, and gdhA genes derived from *Escherichia coli*, and the gltA gene derived from *Brevibacterium lactofermentum*, selecting a strain which is resistant to L-glutamic acid at high concentration and low pH, and selecting a strain which shows superior growth and L-glutamic acid-producing ability.

By culturing the L-glutamic acid-accumulating microorganism in a liquid medium that is adjusted to a pH that allows precipitation of L-glutamic acid, L-glutamic acid can be produced and accumulated while it is precipitated. The "conditions that allow precipitation of L-glutamic acid produced by the microorganism" referred to herein means conditions that allow precipitation of L-glutamic acid when the L-glutamic acid-accumulating microorganism produces and accumulates L-glutamic acid. Although the pH of these conditions may vary depending on the L-glutamic acid-producing ability of the microorganism, it is usually 3 to 5, preferably 4.5 or less, more preferably 4 or less when the microorganism is a bacterium belonging to the genus *Pantoea.*

Furthermore, as for the aforementioned pH condition that allows precipitation of L-glutamic acid, the pH is determined on conditions which allow the L-glutamic acid-accumulating microorganism to metabolize a carbon source in a liquid medium containing L-glutamic acid at a saturation concentration, and exhibit an ability to cause accumulation of L-glutamic acid in the medium in an amount which exceeds the saturation concentration of L-glutamic acid in the medium at that pH.

When the L-glutamic acid-accumulating microorganism is cultured in a medium under the aforementioned conditions, the amount of L-glutamic acid which accumulates can be increased by adding pantothenic acid to the medium. This is presumably because the secondary production of acetoin and 2,3-butanediol is reduced by the addition of pantothenic acid in the medium, and as a result, the fermentation yield of L-glutamic acid is improved.

The pantothenic acid to be contained in the medium is preferably added as a pantothenic acid salt. The amount of the pantothenic acid salt is preferably 1 mg/L or more, more preferably 4 mg/L or more, particularly preferably 8 mg/L or more. The type of pantothenic acid salt is not particularly limited, and examples include calcium salt, sodium salt, and so forth.

Pantothenic acid may be present in the medium during the whole culture process, or only during part of the process. For example, when the method of the present invention comprises the step of proliferating the L-glutamic acid accumulating microorganism and the step of allowing production of L-glutamic acid, pantothenic acid may be present in the medium during at least the step of allowing production of L-glutamic acid, and pantothenic acid may or may not be contained in the medium during the step of proliferating the L-glutamic acid-accumulating microorganism. Furthermore, as for the step of allowing production of L-glutamic acid, the amount of pantothenic acid may not necessarily be within the aforementioned range during the entire time period of this step. That is, pantothenic acid may be present so that the amount is within the aforementioned range during an early part of the step, and the amount may be reduced as the culture progresses. Additional pantothenic acid may also be added intermittently.

Known methods of producing L-glutamic acid using an L-glutamic acid-accumulating microorganism while precipitating L-glutamic acid can be used, except that a medium containing pantothenic acid is used (for example, JP 2001-333769 A (EP 1078989 A), JP 2002-238591 A (EP 1233070 A), JP 2002-238592 A (EP 1233068 A), JP 2002-238593 A (EP 1233069 A)).

For example, one of the preferred embodiments of the method of the present invention is to produce L-glutamic acid by culturing an L-glutamic acid-accumulating microorganism in a medium containing a pantothenic acid salt and having a pH of 5.0 or less, and in which the total content of organic acids that inhibit growth of the microorganism is an amount that does not inhibit the growth of the microorganis (see Japanese Patent Laid-open No. 2002-238591 A (European Patent Laid-open No. 1233070)). In this embodiment, the organic acid that inhibits growth of a microorganism at a pH of a medium means an organic acid that has an inhibitory effect on the growth of the microorganism when it exists at a certain concentration (usually 0.5 g/L or more) in the medium at the pH, and it is usually an organic acid having 1-3 carbons, i.e., formic acid, acetic acid, or propionic acid.

The total content of the organic acid is preferably 0.4 g/L or less, more preferably 0.3 g/L or less, even more preferably 0.2 g/L or less.

Another preferred embodiment of the method of the present invention is to produce an L-glutamic acid which includes culturing an L-glutamic acid-accumulating microorganism at a first pH optimal for growth of the microorganism and then culturing the microorganism at a second pH optimal for production of L-glutamic acid by the microorganism and lower than the first pH, and in which the L-glutamic acid-accumulating bacterium is cultured in a medium containing pantothenic acid during at least the culture at the second pH (see Japanese Patent Laid-open No. 2002-238592 (European Patent Laid-open No. 1233068)).

Another preferred embodiment of the method of the present invention is to produce an L-glutamic acid which includes culturing an L-glutamic acid-accumulating microorganism at a first pH at which growth of the microorganism is not inhibited by organic acids contained in the medium, and then culturing the microorganism at a second pH which is optimal for production of L-glutamic acid by the microorganism and which is lower than the first pH, and wherein the L-glutamic acid-accumulating bacterium is cultured in the medium containing pantothenic acid during at least the culture at the second pH (see Japanese Patent Laid-open No. 2002-238591 (European Patent Laid-open No. 1233070)).

It was found that an L-glutamic acid-producing bacterium was generally inhibited by an organic acid under acidic conditions, whereas it could consume an organic acid under neutral conditions (see Japanese Patent Laid-open No. 2002-238591 (European Patent Laid-open No. 1233070)). Based on this property, by growing the cells at a neutral pH and then changing the pH to be acidic to produce L-glutamic acid, it becomes possible to obtain higher productivity and it also becomes possible to use various materials as a sugar source.

In this embodiment, the "organic acid" means an organic acid that has an inhibitory effect on the growth of the microorganism when it exists at a certain concentration (usually 0.5 g/L or more) in a medium at the second pH, and the organic acid usually has 1-3 carbons, i.e., formic acid, acetic acid, or propionic acid.

The first pH and the second pH are selected so that they meet the properties of the chosen L-glutamic acid-producing bacterium. These pH values can easily be measured by those skilled in the art. For example, the pH at which inhibition of growth of a microorganism is not caused by an organic acid in a medium can be determined by culturing an L-glutamic acid-producing bacterium in a medium containing an organic acid adjusted to various pH values, measuring cell amounts based on absorbance or the like, and comparing the cell amounts with cell amounts of the L-glutamic acid-producing bacterium cultured under the same conditions but in the absence of the organic acid. The pH which is suitable for the production of L-glutamic acid refers to the pH at which L-glutamic acid accumulates in a medium, which is determined by culturing an L-glutamic acid-producing bacterium in media at various pH values. Specifically, it can be determined by measuring amounts of L-glutamic acid which has accumulated in media at various pH values and comparing them.

The first pH is not particularly limited so long as growth of the microorganism is not inhibited by the organic acid in the medium, and it is usually 5.0 to 8.0.

The second pH is preferably a pH at which the produced L-glutamic acid precipitates, and such pH is usually 3.0 to 5.0. Reducing productivity by the accumulation of L-glutamic acid at a high concentration can be obviated by performing the culture at the pH at which the produced L-glutamic acid precipitates.

The first pH and the second pH may not be strictly constant during the culture so long as the advantage of the present invention can be obtained, and they may fluctuate.

The L-glutamic acid-producing bacterium produces L-glutamic acid even at the first pH, and therefore pH is lowered by the produced L-glutamic acid. Therefore, the culture at the first pH is preferably performed while maintaining pH of the medium at the first pH by adding an alkalizing substance to the medium.

Although the alkalizing substance is not particularly limited so long as it does not adversely affect the growth of the L-glutamic acid-producing bacterium or L-glutamic acid production, ammonia gas is preferred.

The pH of the medium may be lowered from the first pH to the second pH by adding an acidic substance. However, pH is lowered by production of L-glutamic acid by the L-glutamic acid-producing bacterium during the culture as described above. Therefore, it is preferable to lower the pH of the medium from the first pH to the second pH by controlling the amount of alkalizing substance which is added, because the addition of the acidic substance can be omitted.

The culture at the first pH may be continued until the organic acid in the medium is depleted. "Depletion" means that the amount of the organic acid decreases to a level at which growth of the L-glutamic acid-producing bacterium is not inhibited during the culture at the second pH. Such a level of the organic acid can be easily measured by those skilled in the art. For example, the level can be determined by culturing an L-glutamic acid-producing bacterium in media containing an organic acid at various concentrations at the second pH, measuring cell amounts of the L-glutamic acid-producing bacterium, and comparing the cell amounts with cell amounts of the L-glutamic acid-producing bacterium cultured under the same conditions but in the absence of the organic acid. Generally, as the second pH becomes lower, the level of the organic acid also becomes lower.

A further preferred embodiment of the method of the present invention is to produce L-glutamic acid by fermentation by culturing an L-glutamic acid-accumulating bacterium in a medium whereby the pH is controlled so that L-glutamic acid which is produced is precipitated to cause accumulation of L-glutamic acid in the medium while precipitating the L-glutamic acid, wherein crystals of L-glutamic acid are induced to exist in the medium during a period wherein the L-glutamic acid concentration in the medium is lower than the concentration at which natural crystallization of L-glutamic acid occurs, and the medium contains pantothenic acid (see Japanese Patent Laid-open No. 2002-238593 (European Patent Laid-open No. 1233069)). The "natural crystallization" means that, when a microorganism having an ability to produce L-glutamic acid accumulates L-glutamic acid, the L-glutamic acid concentration in the medium exceeds the saturation concentration of L-glutamic acid, and thus L-glutamic acid naturally precipitates in the medium.

To make crystals of L-glutamic acid exist in the medium means artificially providing the crystals of L-glutamic acid in the medium. Examples of include adding crystals, dissolving a certain amount of L-glutamic acid in the medium at the start of the culture, and decreasing the pH during the culture to forcibly precipitate crystals, and so forth. The amount of crystals made to exist in the medium is usually 0.01 to 10 g/L. Furthermore, the period where the crystals are made to exist is preferably a period where the amount of accumulated L-glutamic acid in the medium increases to a concentration around the saturation concentration (for example, when pH is 4.5 or higher, 25 g/L or more). The amount of L-glutamic acid crystals that exist in the medium and the concentration of L-glutamic acid can be measured by methods well known to those skilled in the art. Crystals of L-glutamic acid are measured after the medium is left standing, and the crystals are collected by decantation. The concentration of L-glutamic acid in the medium is a concentration of dissolved L-glutamic acid. When crystals precipitate in the medium, the concentration of L-glutamic acid means the L-glutamic acid concentration which is measured in a clear solution obtained by separating solid content from the medium by centrifugation (or filtration).

Making the crystals of L-glutamic acid exist in the medium is preferably done by the addition of the crystals of L-glutamic acid.

Crystals of L-glutamic acid include those of α-form and β-form (H. Takahashi, T. Takenishi, N. Nagashima, Bull. Chem. Soc. Japan, 35, 923 (1962); J. D. Bernal, Z. Krist., 78, 363 (1931); S. Hirokawa, Acta Cryst., 8, 637 (1955)). When crystals of the α-form are to be obtained, the crystals to be added are preferably those of the α-form.

The preferred amount of crystals to be added varies depending on the conditions, including the form of the crystals and so forth, and it is usually 0.2 g/L or more for the α-form crystals. If the crystals are added in the aforementioned amount or a larger amount, α-form crystals can be obtained with good reproducibility. Crystals of α-form can be handled more easily than compared with crystals of the β-form in view of the morphology thereof.

As the medium used for the present invention, a usual nutrient medium containing a carbon source, nitrogen source, and inorganic salts as well as organic trace amount nutrients such as amino acids and vitamins as required can be used, except that it contains pantothenic acid, and the pH is adjusted to satisfy the predetermined conditions. Either a synthetic medium or natural medium may be used. Any carbon source and nitrogen source that can be used by the chosen strain may be used in the medium.

Saccharides such as glucose, glycerol, fructose, sucrose, maltose, mannose, galactose, starch hydrolysate, and molasses can be used as the carbon source. In addition, organic acids such as acetic acid and citric acid may be used alone or in combination with another carbon source.

Ammonia, ammonium salts such as ammonium sulfate, ammonium carbonate, ammonium chloride, ammonium phosphate and ammonium acetate, nitrates, and so forth are used as the nitrogen source.

Amino acids, vitamins, fatty acids, nucleic acids, and those containing these substances such as peptone, casamino acid, yeast extract, and soybean protein decomposition products are used as the organic trace nutrients. When an auxotrophic mutant strain that requires an amino acid and so forth for metabolization or growth is used, the required nutrient must be supplemented.

Phosphates, magnesium salts, calcium salts, iron salts, manganese salts, and so forth are used as mineral salts.

As for the culture method, an aeration culture at 20 to 42° C. is usually performed provided that the pH is controlled to be a predetermined value, preferably 3 to 5.

After completion of the culture, the L-glutamic acid which has precipitated in the culture can be collected by centrifugation, filtration, or the like. L-Glutamic acid dissolved in the medium can be also collected by known methods. For example, the L-glutamic acid can be isolated by concentrating the culture broth to crystallize it or isolated by ion exchange chromatography or the like. It is also possible to crystallize L-glutamic acid dissolved in the medium and then collect the crystallized L-glutamic acid along with the L-glutamic acid precipitated during the culture.

When the L-glutamic acid exceeds the saturation concentration and precipitates, the concentration of L-glutamic acid dissolved in the medium is maintained at a constant level. Therefore, the effect of a high concentration of L-glutamic acid on microorganisms can be reduced. Accordingly, it also becomes possible to breed a microorganism which has even better L-glutamic acid-producing ability. Furthermore, since L-glutamic acid is precipitated as crystals, acidification of the culture broth by accumulation of L-glutamic acid is suppressed, and therefore the amount of alkali which needs to be used for maintaining the pH of the culture can significantly be reduced.

EXAMPLES

Hereafter, the present invention will be more specifically explained with reference to the following non-limited examples.

Reference Example 1

<1> Screening of Microorganism Having L-Glutamic Acid Resistance in Acidic Environment Screening of a microorganism having L-glutamic acid resistance in an acidic environment was performed as follows. One (1) g each of about 500 samples obtained from nature including soil, fruits, plant bodies, river water, and so forth was suspended in 5 mL of sterilized water, and 200 μL thereof was applied on 20 mL of solid medium adjusted to pH 4.0 with HCl. The composition of the medium was as follows: 3 g/L of glucose, 1 g/L of ammonium sulfate, 0.2 g/L of magnesium sulfate heptahydrate, 0.5 g/L of potassium dihydrogenphosphate, 0.2 g/L of sodium chloride, 0.1 g/L of calcium chloride dihydrate, 0.01 g/L of ferrous sulfate heptahydrate, 0.01 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 50 μg/L of biotin, 50 μg/L of calcium pantothenate, 50 μg/L of folic acid, 50 μg/L of inositol, 50 μg/L of niacin, 50 μg/L of p-aminobenzoic acid, 50 μg/L of pyridoxine hydrochloride, 50 μg/L of riboflavin, 50 μg/L of thiamin hydrochloride, 50 mg/L of cycloheximide, and 20 g/L of agar.

The media plated with the above samples were incubated at 28° C., 37° C., or 50° C. for 2 to 4 days, and 378 colony-forming strains were obtained.

Subsequently, each of the strains obtained as described above was inoculated in a test tube of 16.5 cm in length and 14 mm in diameter containing 3 mL of liquid medium (adjusted to pH 4.0 with HCl) which contained L-glutamic acid at a saturation concentration, and cultured at 28° C., 37° C., or 50° C. for 24 hours to 3 days with shaking. Then, the strains which grew were selected. The composition of the aforementioned medium was follows: 40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, and 2 g/L of yeast extract.

Thus, 78 strains of microorganisms which showed L-glutamic acid resistance in an acidic environment were successfully obtained.

<2> Selection of the Strains Showing a Superior Growth Rate from Microorganisms Having L-Glutamic Acid Resistance in an Acidic Environment The various microorganisms having L-glutamic acid resistance in an acidic environment obtained as described above are each inoculated into a test tube of 16.5 cm in length and 14 mm in diameter containing 3 mL of medium (adjusted to pH 4.0 with HCl) obtained by adding 20 g/L of glutamic acid and 2 g/L of glucose to M9 medium (Sambrook, J., Fritsh, E. F. and Maniatis, T., "Molecular Cloning", Cold Spring Harbor Laboratory Press, U.S.A., 1989), and the turbidity of the medium was measured over time, so to select strains showing a favorable growth rate. As a result, the AJ13355 strain was obtained from soil in Iwata-shi, Shizuoka, Japan which showed a favorable growth rate. This strain was determined to be *Enterobacter agglomerans* based on its bacteriological properties described above. *Enterobacter agglomerans* includes those re-classified into *Pantoea agglomerans, Pantoea ananatis, Pantoea stewartii*, and so forth on the basis of nucleotide sequence analysis of 16S rRNA or the like, and the AJ13355 strain is classified into *Pantoea ananatis* among these.

<3> Acquisition of a Strain with Reduced Mucus Secretion from *Pantoea ananatis* AJ13355 Strain Since the *Pantoea ananatis* AJ13355 strain secretes mucus extracellularly when cultured in a medium containing a saccharide, operation efficiency is not favorable. Therefore, a strain with reduced mucus secretion was obtained by the ultraviolet irradiation method (Miller, J. H. et al., "A Short Course in Bacterial Genetics; Laboratory Manual", p. 150, 1992, Cold Spring Harbor Laboratory Press, U.S.A.).

The *Pantoea ananatis* AJ13355 strain was irradiated with an ultraviolet ray for 2 minutes at a position 60 cm away from a 60-W ultraviolet lamp and cultured in LB medium overnight to fix the mutation. The mutagenized strain was diluted and inoculated in LB medium containing 5 g/L of glucose and 20 g/L of agar so that about 100 colonies per plate emerged, and was cultured at 30° C. overnight while the plate was tilted at about 45 degrees, and then 20 colonies without mucus flow were selected.

As a strain for which no revertant emerged even after subculturing 5 times in LB medium containing 5 g/L of glucose and 20 g/L of agar, and which showed growth equivalent to the parent strain in LB medium, LB medium containing 5 g/L of glucose and M9 medium (Sambrook, J. et al., Molecular Cloning, 2nd Edition, Cold Spring Harbor Press, U.S.A., 1989) supplemented with 20 g/L of L-glutamic acid and 2 g/L of glucose and adjusted to pH 4.5 with HCl, the SC17 strain was selected from the strains selected above.

<4> Construction of Glutamic Acid-Producing Bacterium from *Pantoea ananatis* $SC_{17}$ Strain (1) Preparation of αKGDH Deficient Strain from *Pantoea ananatis* SC17 Strain A strain that was deficient in αKGDH and had enhanced L-glutamic acid biosynthetic system was prepared from the *Pantoea ananatis* SC17 strain.

(i) Cloning of αKGDH Gene (Hereinafter, Referred to as "sucAB") of *Pantoea ananatis* AJ13355 Strain The sucAB gene of the *Pantoea ananatis* AJ13355 strain was cloned by selecting a DNA fragment complementing the acetic acid-unassimilating property of the αKGDH-E 1 subunit gene (hereafter, referred to as "sucA")-deficient strain of *Escherichia coli* from chromosomal DNA of the *Pantoea ananatis* AJ13355 strain.

The chromosomal DNA of the *Pantoea ananatis* AJ13355 strain was isolated by a method usually employed for extracting chromosomal DNA from *Escherichia coli* (Text for Bioengineering Experiments, Edited by the Society for Bioscience and Bioengineering, Japan, pp. 97-98, Baifukan, 1992). The pTWV228 (resistant to ampicillin), which is a commercial product of Takara Shuzo Co., Ltd, and was used as a vector.

The chromosomal DNA of the AJ13355 strain digested with EcoT221 and pTWV228 which had been digested with PstI were ligated using T4 ligase, and the ligation mixture was used to transform the sucA-deficient *Escherichia coli* JRG465 strain (Herbert, J. et al., Mol. Gen. Genetics, 105, 182 (1969)). A strain able to grow in an acetate minimal medium was selected from the transformant strains obtained above, and a plasmid was extracted from the obtained strain and designated pTWVEK101. The *Escherichia coli* JRG465 strain harboring pTWVEK101 recovered auxotrophy for succinic acid or L-lysine and L-methionine, besides the trait of acetic acid-unassimilating property. This suggests that pTWVEK101 contained the sucA gene of *Pantoea ananatis*.

FIG. 1 shows a restriction enzyme map of a DNA fragment derived from *Pantoea ananatis* in pTWVEK101. In the nucleotide sequence of the hatched portion in FIG. 1, nucleotide sequences considered to be two full length ORFs and two nucleotide sequences considered to be partial sequences of ORFs were found. Amino acid sequences which are predicted to be encoded by these ORFs or the partial sequences are shown in SEQ ID NOS: 2-5 starting from 5' side. As a result of homology search, portions of the nucleotide sequences were determined to contain a 3' end partial sequence of the succinate dehydrogenase iron-sulfur protein gene (sdhB), full length sucA and αKGDH-E2 subunit gene (sucB), and a 5' end partial sequence of the succinyl CoA synthetase β subunit gene (sucC). A comparison of the amino acid sequences deduced from these nucleotide sequences with those derived from *Escherichia coli* (Eur. J. Biochem., 141, pp. 351-359 (1984); Eur. J. Biochem., 141, pp. 361-374 (1984); Biochemistry, 24, pp. 6245-6252 (1985)) showed that these amino acid sequences are very high homolous to each other. In addition, it was found that a cluster of sdhB-sucA-sucB-sucC was located on the chromosome of *Pantoea ananatis*, as in *Escherichia coli* (Eur. J. Biochem., 141, pp. 351-359 (1984); Eur. J. Biochem., 141, pp. 361-374 (1984); Biochemistry, 24, pp. 6245-6252 (1985)).

(ii) Acquisition of αKGDH-Deficient Strain Derived from *Pantoea ananatis* SC17 Strain The homologous recombination was performed using the sucAB gene of *Pantoea ananatis* obtained as described above to obtain an αKGDH-deficient strain of *Pantoea ananatis*.

After pTWVEK101 was digested with SphI to excise a fragment containing sucA, the fragment was blunt-ended with Klenow fragment (Takara Shuzo Co., Ltd.) and ligated with pBR322 which had been digested with EcoRI and blunt-ended with Klenow fragment, by using T4 DNA ligase (Takara Shuzo Co., Ltd.). The obtained plasmid was digested at the restriction enzyme BglII recognition site, located approximately at the center of sucA by using the enzyme, blunt-ended with Klenow fragment, and then ligated again by using T4 DNA ligase. It was thought that the sucA gene was unable to function due to the introduction of a frameshift mutation into sucA on the newly constructed plasmid during the above procedure.

The plasmid constructed as described above was digested with a restriction enzyme ApaLI, and subjected to agarose gel electrophoresis to recover a DNA fragment containing sucA into which the frameshift mutation was introduced and a tetracycline resistance gene derived from pBR322. The recovered DNA fragment was ligated again using T4 DNA ligase to construct a plasmid for disrupting the αKGDH gene.

The plasmid for disrupting the αKGDH gene obtained as described above was used to transform the *Pantoea ananatis* SC17 strain by electroporation (Miller, J. H., "A Short Course in Bacterial Genetics; Handbook", p. 279, Cold Spring Harbor Laboratory Press, U.S.A., 1992), and a strain wherein sucA on the chromosome was replaced with a mutant sucA of the plasmid by homologous recombination was obtained using the tetracycline resistance as a marker. This strain was designated SC17sucA.

In order to confirm that the SC17sucA strain was deficient in αKGDH activity, the enzyme activity was measured by the method of Reed et al. (Reed, L. J. and Mukherjee, B. B., Methods in Enzymology, 13, pp. 55-61, (1969)) using cells of the strain cultured in LB medium to the logarithmic growth phase. As a result, αKGDH activity of 0.073 (ΔABS/min/mg protein) was detected from the SC17 strain, whereas no αKGDH activity was detected from the SC17sucA strain, and thus it was confirmed that the sucA was eliminated as intended.

(2) Enhancement of L-Glutamic Acid Biosynthesis System of *Pantoea ananatis* SC17sucA Strain Subsequently, the citrate synthase gene, phosphoenolpyruvate carboxylase gene and glutamate dehydrogenase gene derived from *Escherichia coli* were introduced into the SC17sucA strain.

(i) Preparation of a Plasmid Having the gltA Gene, ppc Gene, and gdhA Gene, all Derived from *Escherichia coli*

Figure 2:
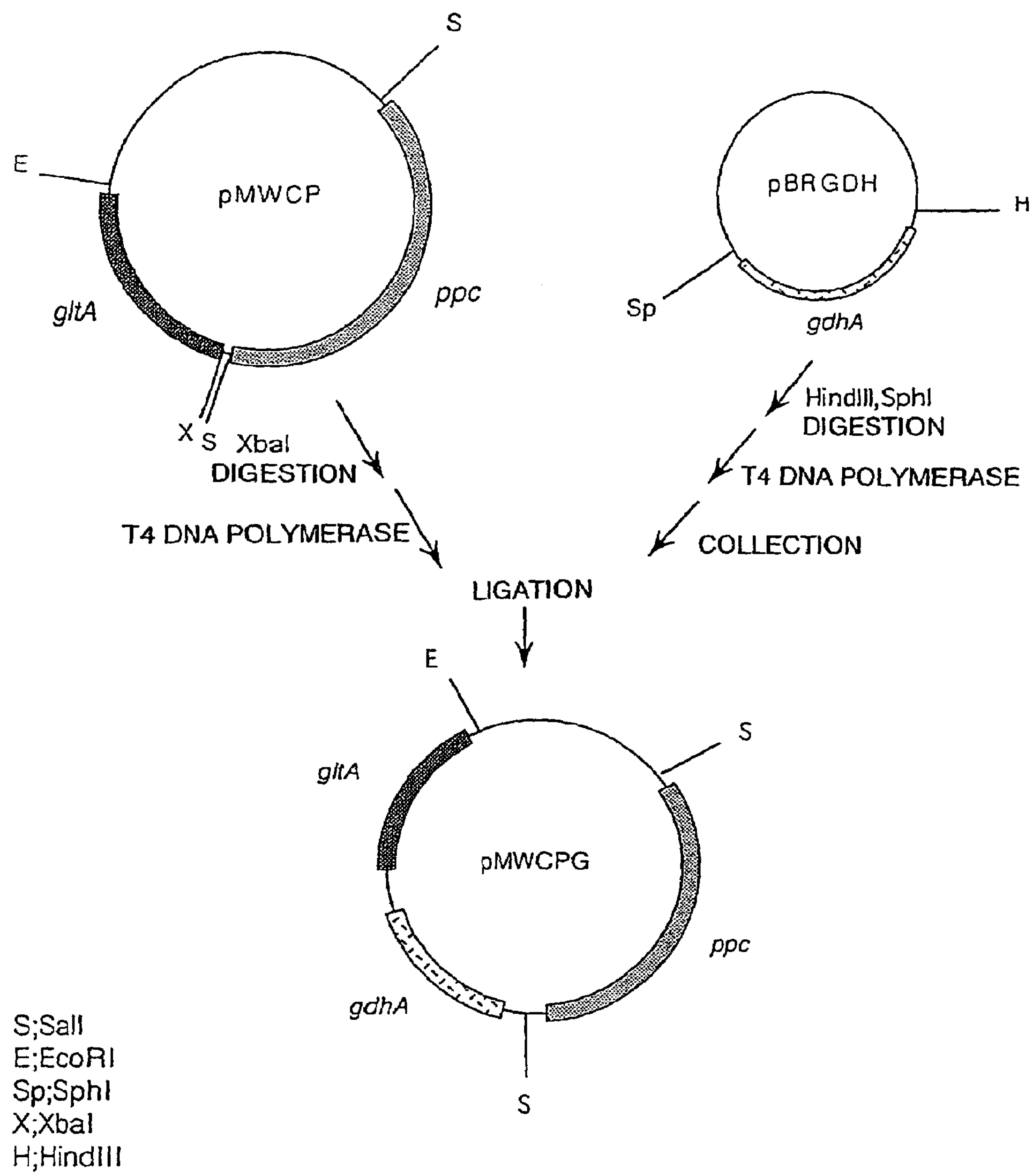
FIG. 2 shows construction of a plasmid pMWCPG containing genes gltA, ppc and gdhA.
Figure 3:
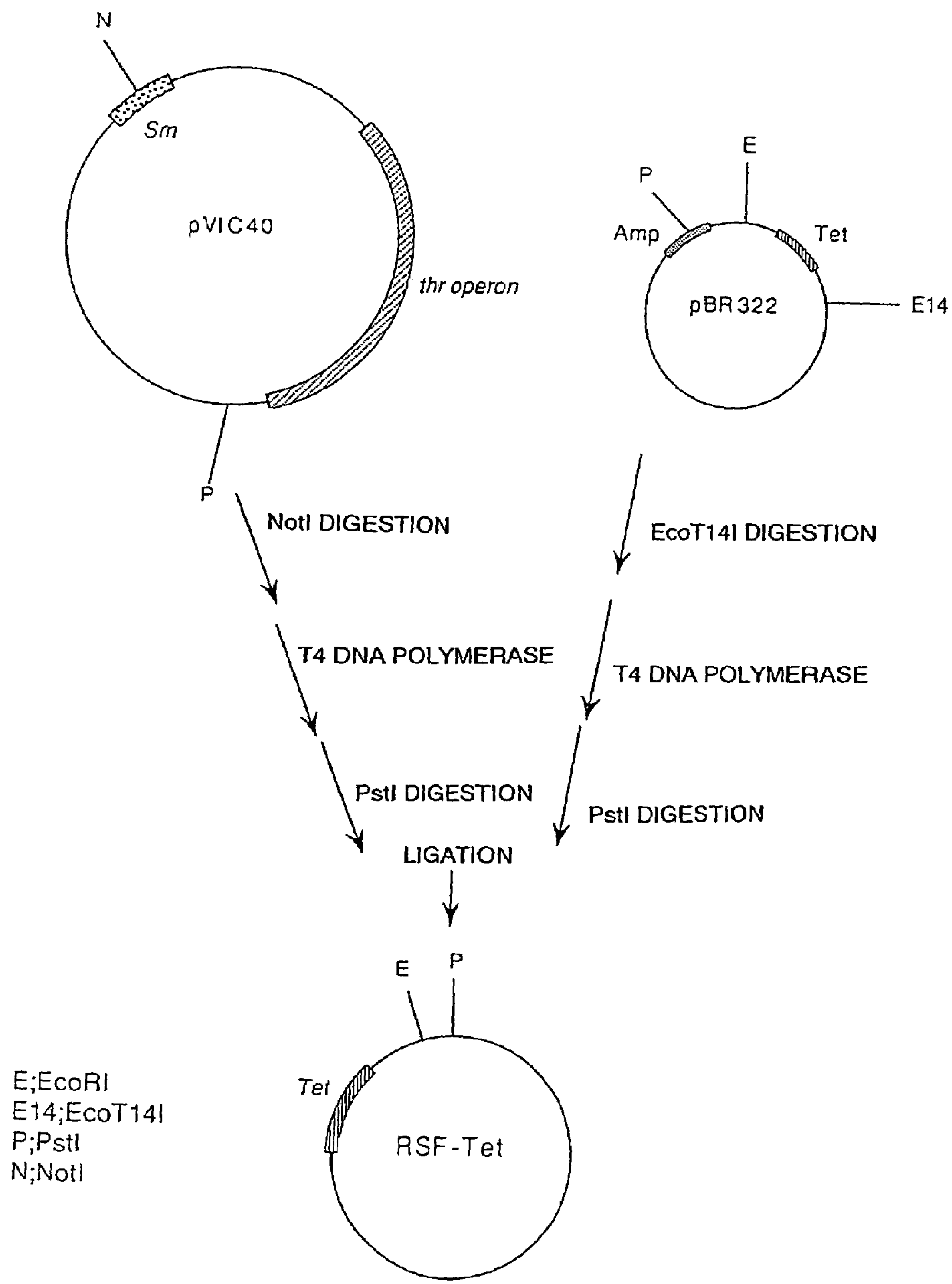
FIG. 3 shows construction of a plasmid RSF-Tet containing the replication origin of the wide host range plasmid RSF1010 and tetracycline resistence gene.

The procedures for preparing a plasmid having the gltA gene, the ppc gene, and the gdhA gene will be explained by referring to FIGS. 2 and 3.

A plasmid having the gdhA gene derived from *Escherichia coli*, pBRGDH (JP 7-203980 A), was digested with HindIII and SphI, and both ends were blunt-ended by treating with T4 DNA polymerase, and then the DNA fragment having the gdhA gene was purified and recovered. Separately, a plasmid having the gltA gene and ppc gene derived from *Escherichia coli*, pMWCP (WO97/08294), was digested with XbaI, and then both ends were blunt-ended with T4 DNA polymerase. This was mixed with the above purified DNA fragment having the gdhA gene and ligated using T4 ligase to obtain the plasmid pMWCPG, which is pMWCP with the addition of the gdhA gene (FIG. 2).

Concurrently, the plasmid pVIC40 (Japanese Patent Laid-open No. 8-047397) having the replication origin of the wide-host-range plasmid RSF1010 was digested with NotI, treated with T4 DNA polymerase, and digested with PstI. pBR322 was digested with EcoT14I, treated with T4 DNA polymerase and digested with PstI. Both products were mixed and ligated using T4 ligase to obtain a plasmid RSF-Tet having the replication origin of RSF1010 and the tetracycline resistance gene (FIG. 3).

Figure 4:
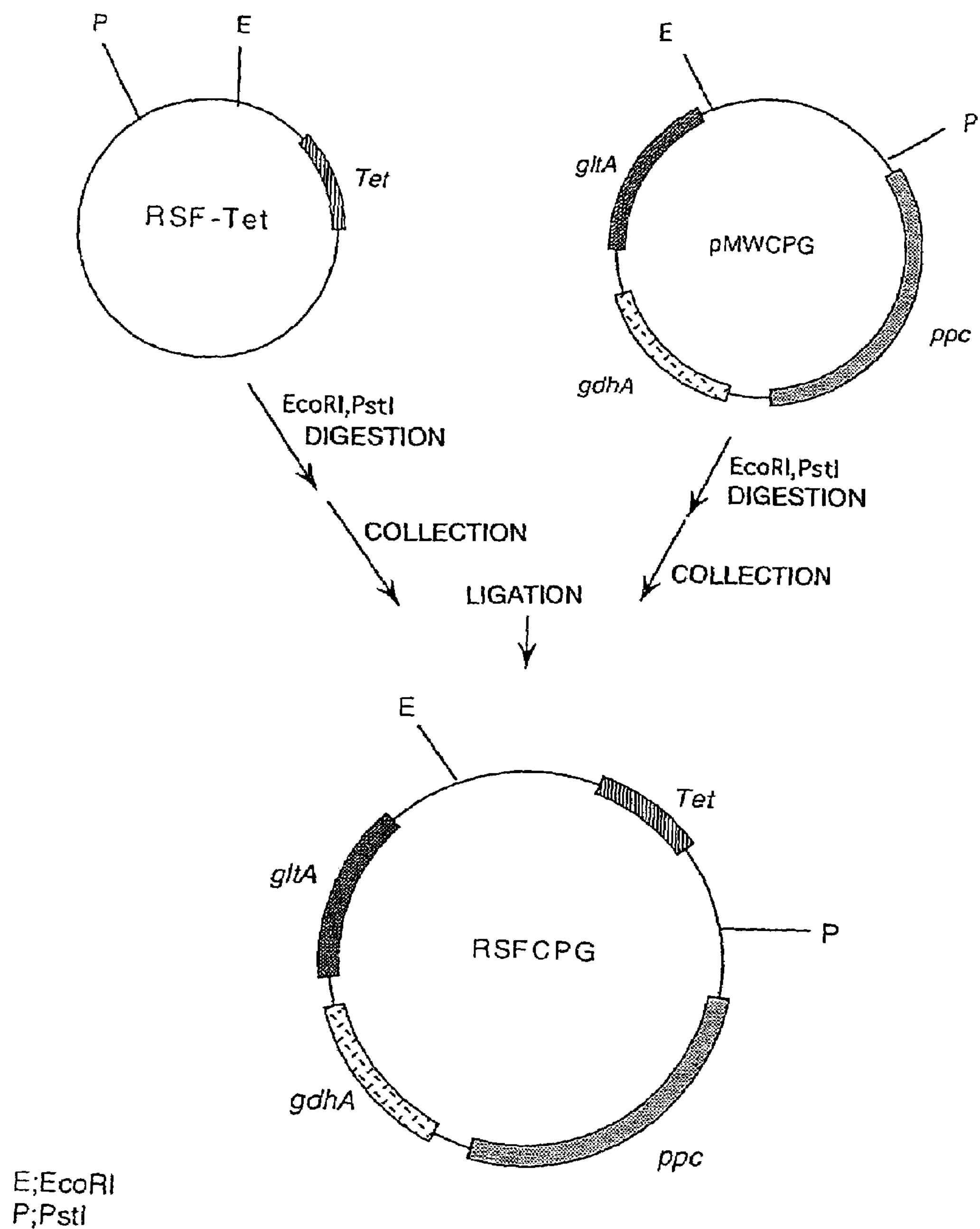
FIG. 4 shows construction of a plasmid RSFCPG containing the replication origin of the wide host range plasmid RSF1010, tetracycline resistance gene, gltA gene, ppc gene and gdhA gene.

Subsequently, pMWCPG was digested with EcoRI and PstI, and a DNA fragment having the gltA gene, the ppc gene, and the gdhA gene was purified and recovered. RSF-Tet was similarly digested with EcoRI and PstI, and a DNA fragment having the replication origin of RSF1010 was purified and recovered. Both products were mixed and ligated using T4 ligase to obtain a plasmid RSFCPG, which corresponded to RSF-Tet containing the gltA gene, the ppc gene, and the gdhA gene (FIG. 4). It was confirmed that the obtained plasmid RSFCPG expressed the gltA gene, the ppc gene, and the gdhA gene based on the supplementation of the auxotrophy of the gltA gene-, ppc gene-, or gdhA gene-deficient strain derived from *Escherichia coli* and measurement of each enzyme activity.

(ii) Preparation of Plasmid Having gltA Gene Derived from *Brevibacterium Lactofermentum*

Figure 5:
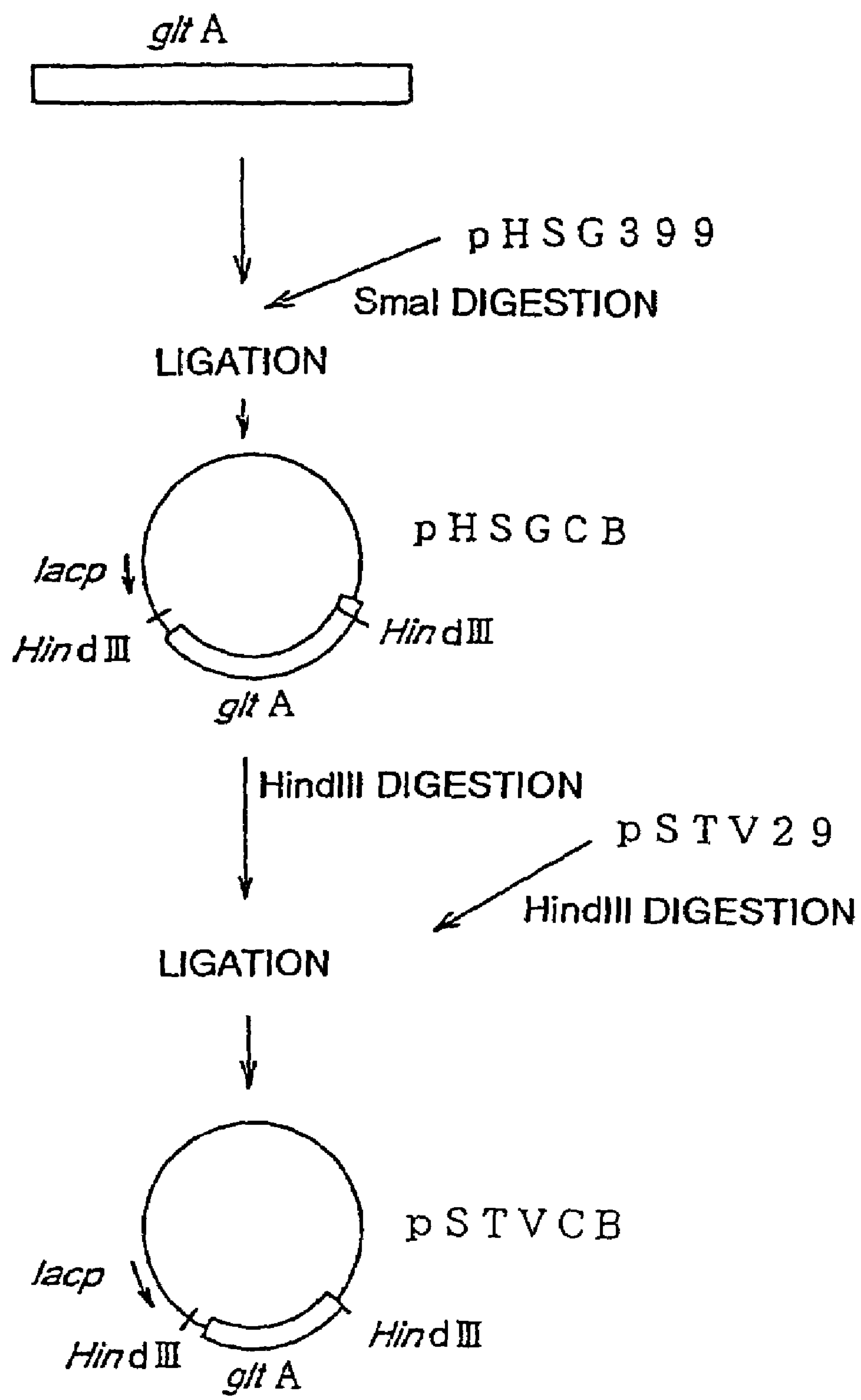
FIG. 5 shows construction of a plasmid pSTVCB containing the gltA gene.

A plasmid having the gltA gene derived from *Brevibacterium lactofermentum* was constructed as follows. PCR was performed using primers having nucleotide sequences SEQ ID NOS:6 and 7 which were prepared based on the nucleotide sequence of the *Corynebacterium glutamicum* gltA gene (Microbiology, 140, pp. 1817-1828 (1994)), and chromosomal DNA of *Brevibacterium lactofermentum* ATCC13869 was used as a template to obtain a gltA gene fragment of about 3 kb. This fragment was inserted into a plasmid pHSG399 (purchased from Takara Shuzo Co., Ltd.) which had been digested with SmaI to obtain a plasmid pHSGCB (FIG. 5). Subsequently, pHSGCB was digested with HindIII, and the excised gltA gene fragment of about 3 kb was inserted into the plasmid pSTV29 (purchased from Takara Shuzo Co., Ltd.) digested with HindIII to obtain a plasmid pSTVCB (FIG. 5). It was confirmed that the obtained plasmid pSTVCB expressed the gltA gene by measuring the enzyme activity in the *Pantoea ananatis* AJ 13355 strain.

(iii) Introduction of RSFCPG and pSTVCB into SC17sucA Strain

The *Pantoea ananatis* SC17sucA strain was transformed with RSFCPG by electroporation to obtain a transformant SC17sucA/RSFCPG strain which was resistant to tetracycline. Furthermore, the SC17sucA/RSFCPG strain was transformed with pSTVCB by electroporation to obtain a transformant SC17sucA/RSFCPG+pSTVCB strain showing chloramphenicol resistance.

<4> Acquisition of a Strain with Improved Resistance to L-Glutamic Acid in a Low pH Environment A strain with improved resistance to L-glutamic acid at high concentrations in a low pH environment (hereafter, also referred to as "strain with high-concentration Glu-resistance at low pH") was isolated from the *Pantoea ananatis* SC17sucA/RSFCPG+pSTVCB strain.

The SC17sucA/RSFCPG+pSTVCB strain was cultured overnight at 30° C. in LBG medium (10 g/L of trypton, 5 g/L of yeast extract, 10 g/L of NaCl, 5 g/L of glucose), and the cells washed with saline was appropriately diluted and plated on an M9-E medium (4 g/L of glucose, 17 g/L of $Na_2HPO_4.12H_2O$, 3 g/L of $KH_2PO_4$, 0.5 g/L of NaCl, 1 g/L of $NH_4Cl$, 10 mM of $MgSO_4$, 10 μM of $CaCl_2$, 50 mg/L of L-lysine, 50 mg/L of L-methionine, 50 mg/L of DL-diaminopimelic acid, 25 mg/L of tetracycline, 25 mg/L of chloramphenicol, 30 g/L of L-glutamic acid, adjusted to pH 4.5 with aqueous ammonia) plate. A colony was obtained which emerged after culture at 32° C. for 2 days as a strain with high-concentration Glu-resistance at low pH.

For the obtained strain, the growth level in M9-E liquid medium was measured and L-glutamic acid-producing ability was tested in a 50-ml volume large test tube containing 5 ml of L-glutamic acid production test medium (40 g/L of glucose, 20 g/L of ammonium sulfate, 0.5 g/L of magnesium sulfate heptahydrate, 2 g/L of potassium dihydrogenphosphate, 0.5 g/L of sodium chloride, 0.25 g/L of calcium chloride dihydrate, 0.02 g/L of ferrous sulfate heptahydrate, 0.02 g/L of manganese sulfate tetrahydrate, 0.72 mg/L of zinc sulfate dihydrate, 0.64 mg/L of copper sulfate pentahydrate, 0.72 mg/L of cobalt chloride hexahydrate, 0.4 mg/L of boric acid, 1.2 mg/L of sodium molybdate dihydrate, 2 g/L of yeast extract, 200 mg/L of L-lysine hydrochloride, 200 mg/L of L-methionine, 200 mg/L of DL-α,ε-diaminopimelic acid, 25 mg/L of tetracycline hydrochloride, and 25 mg/L of chloramphenicol). A strain that exhibited the best growth level and the same L-glutamic acid-producing ability as that of its parent strain, the SC17/RSFCPG+pSTVCB strain, was designated *Pantoea ananatis* AJ13601. The AJ13601 strain was deposited at the National Institute of Bioscience and Human-Technology, Agency of Industrial Science and Technology, Ministry of International Trade and Industry (currently, National Institute of Advanced Industrial Science and Technology, International Patent Organism Depositary, Central 6, 1-1, Higashi 1-Chome, Tsukuba-shi, Ibaraki-ken, 305-8566, Japan) on Aug. 18, 1999 and received an accession number of FERM P-17516. It was then converted to an international deposit under the provisions of Budapest Treaty on Jul. 6, 2000 and received an accession number of FERM BP-7207.

Example 1

The *Pantoea ananatis* AJ13601 strain was cultured in a medium containing calcium pantothenate (12 mg/L) and also in a medium not containing calcium pantothenate to investigate the production of L-glutamic acid.

Specifically, the culture was performed as follows. Cells of the *Pantoea ananatis* AJ13601 strain cultured at 30° C. for 14 hours in the LBG agar medium (10 g/L of trypton, 5 g/L of yeast extract, 10 g/L of NaCl, 15 g/L of agar) containing 25 mg/L of tetracycline hydrochloride and 25 mg/L of chloramphenicol were scraped from one plate and inoculated into 300 ml of seed culture medium having the following composition and contained in a 1 L-volume jar fermenter, and seed culture was performed under conditions of 34° C. and pH 6.0.

Composition of seed culture medium:

| | |
|---|---|
| Sucrose | 50 g/L |
| MgSO4•7H2O | 0.4 g/L |
| KH2PO4 | 2.0 g/L |
| Yeast extract | 4.0 g/L |
| FeSO4•7H2O | 0.01 g/L |
| MnSO4•5H2O | 0.01 g/L |
| L-Lysine hydrochloride | 0.4 g/L |
| DL-Methionine | 0.4 g/L |
| ε-Diaminopimelic acid | 0.4 g/L |
| Tetracycline hydrochloride | 25 mg/L |
| Chloramphenicol | 25 mg/L |

The pH was adjusted to 6.0 by adding ammonia gas during the culture. The seed culture was finished when depletion of the saccharide in the medium was observed, and the seed culture medium corresponding to 20% volume of the main culture medium was inoculated to 300 ml of the main culture medium contained in a 1 L-volume jar fermenter to perform the main culture under conditions of 34° C. and pH 4.5. The composition of the main culture medium is shown below.

Composition of main culture medium:

| | |
|---|---|
| Glucose | 50 g/L |
| (NH4)2SO4 | 5.0 g/L |
| MgSO4•7H2O | 0.4 g/L |
| KH2PO4 | 6.0 g/L |
| NaCl | 1.5 g/L |
| FeSO4•7H2O | 0.01 g/L |
| MnSO4•5H2O | 0.01 g/L |
| L-Lysine hydrochloride | 0.8 g/L |
| DL-Methionine | 0.6 g/L |
| DL-α,ε-Diaminopimelic acid | 0.6 g/L |
| Tetracycline hydrochloride | 25 mg/L |
| Chloramphenicol | 25 mg/L |
| Calcium chloride dihydrate | 0.75 g/L |
| Calcium pantothenate (added only for the culture with pantothenic acid) | 12 mg/L |

The pH was adjusted to 4.5 by adding ammonia gas during the culture. After the saccharide in the medium was consumed and depleted, a 700 g/L of glucose aqueous solution was continuously added (5 ml/hr). When the L-glutamic acid concentration in the culture broth reached 45 g/L, 1.0 g/L of L-glutamic acid crystals were added to the medium as seed crystals to promote precipitation of L-glutamic acid in the culture broth.

After the main culture was performed for 50 hours, a marked amount of L-glutamic acid crystals were precipitated in the jar fermenter. Then, ammonia gas was added to raise pH to 6.0 and thereby dissolve all the L-glutamic acid crystals in the jar fermenter. Then, the amount of the produced L-glutamic acid was measured. The L-glutamic acid concentration was measured by using Automatic enzyme electrode analyzer As210 produced by Asahi Chemical Industry.

As a result, it was found that the L-glutamic acid fermentation yield was significantly improved by the addition of pantothenic acid, as shown in Table 1.

TABLE 1

| | No addition of calcium pantothenate | With addition of calcium pantothenate (12 mg/L) |
|---|---|---|
| L-Glutamic acid fermentation yield (%) | 40.2 | 53.3 |

The cause of the improvement of the L-glutamic acid yield provided by the addition of calcium pantothenate was investigated. As a result, reduction of acetoin, 2,3-butanediol and $CO_2$ production was confirmed (Table 2). The acetoin and 2,3-butanediol concentrations were measured by using a gas chromatography apparatus GC 1700 produced by Shimadzu with the following conditions.

Column used:

DB-210 123-0233 produced by J & W Scientific, column length: 30 m, column diameter: 0.32 mm, film thickness: 5 μm Measurement conditions:

Temperature of vaporization chamber: 250° C.
Carrier gas: He
Pressure: 85.6 kPa
Total flow rate: 97.2 ml/min
Column flow rate: 0.93 ml/min
Linear velocity: 25.0 cm/sec
Purge flow rate: 3.0 ml/min
Split ratio: 100
Column temperature: 70° C.
Makeup gas: He
Makeup flow rate: 30.0 ml/min
$H_2$ flow rate: 47 ml/min
Air flow rate: 400 ml/min The discharged $CO_2$ amount was measured using an Exhaust oxygen carbon dioxide meter Model EX-1562 produced by ABLE. The produced amounts of acetoin and 2,3-butanediol as well as the produced amount of $CO_2$ calculated from these values are shown in Table 2 (all values are represented in terms of carbon amount). The measured values of $CO_2$ discharged from the culture medium were 26.5% with no pantothenic acid and 27.6% with pantothenic acid.

When calcium pantothenate was added to the medium, the amounts of acetoin, 2,3-butanediol, and $CO_2$ generated in association with the secondary production of the foregoing substances (two moles of $CO_2$ is generated for 1 mole each of acetoin and 2,3-butanediol) were reduced by about 14.3% in terms of the carbon balance compared with when calcium pantothenate was not added. Because this value is substantially equivalent to the difference between the L-glutamic acid fermentation yields obtained with and without addition of calcium pantothenate, i.e., about 13.1%, it is considered that the yield improvement effect provided by the addition of calcium pantothenate was mainly caused by reduction of the secondary production of acetoin and 2,3-butanediol.

TABLE 2

| Secondary product (%, in terms of carbon) | No addition of calcium pantothenate | With addition of calcium pantothenate (12 mg/L) |
|---|---|---|
| Acetoin + $CO_2$ generated in association with production of acetoin | 12.0 | 2.5 |
| Butanediol + $CO_2$ generated in association with production of butanediol | 6.1 | 1.3 |

From the above results, the mechanism of the improvement of L-glutamic acid fermentation yield provided by the addition of pantothenic acid was estimated as follows. That is, it is considered that the L-glutamic acid fermentation yield was improved because insufficiency of coenzyme A (CoA) could be compensated by the addition of pantothenic acid. Pantothenic acid is contained in the structure of CoA in the form of pantetheine, and thus it is one of the constituents of CoA. CoA is used as a coenzyme in the process of converting pyruvic acid into acetyl-CoA in the metabolic pathway. On the other hand, acetoin and 2,3-butanediol are generated from pyruvic acid, and $CO_2$ is discharged in association with the production of acetoin. When pantothenic acid was not added to the medium used for the culture of the L-glutamic acid-producing bacterium, acetoin and 2,3-butanediol accumulated in the medium. Therefore, it is considered that CoA was originally insufficient in the bacterium, and sufficient acetyl-CoA was not produced in the bacterium, which resulted in the secondary production of acetoin and 2,3-butanediol.

Figure 6:
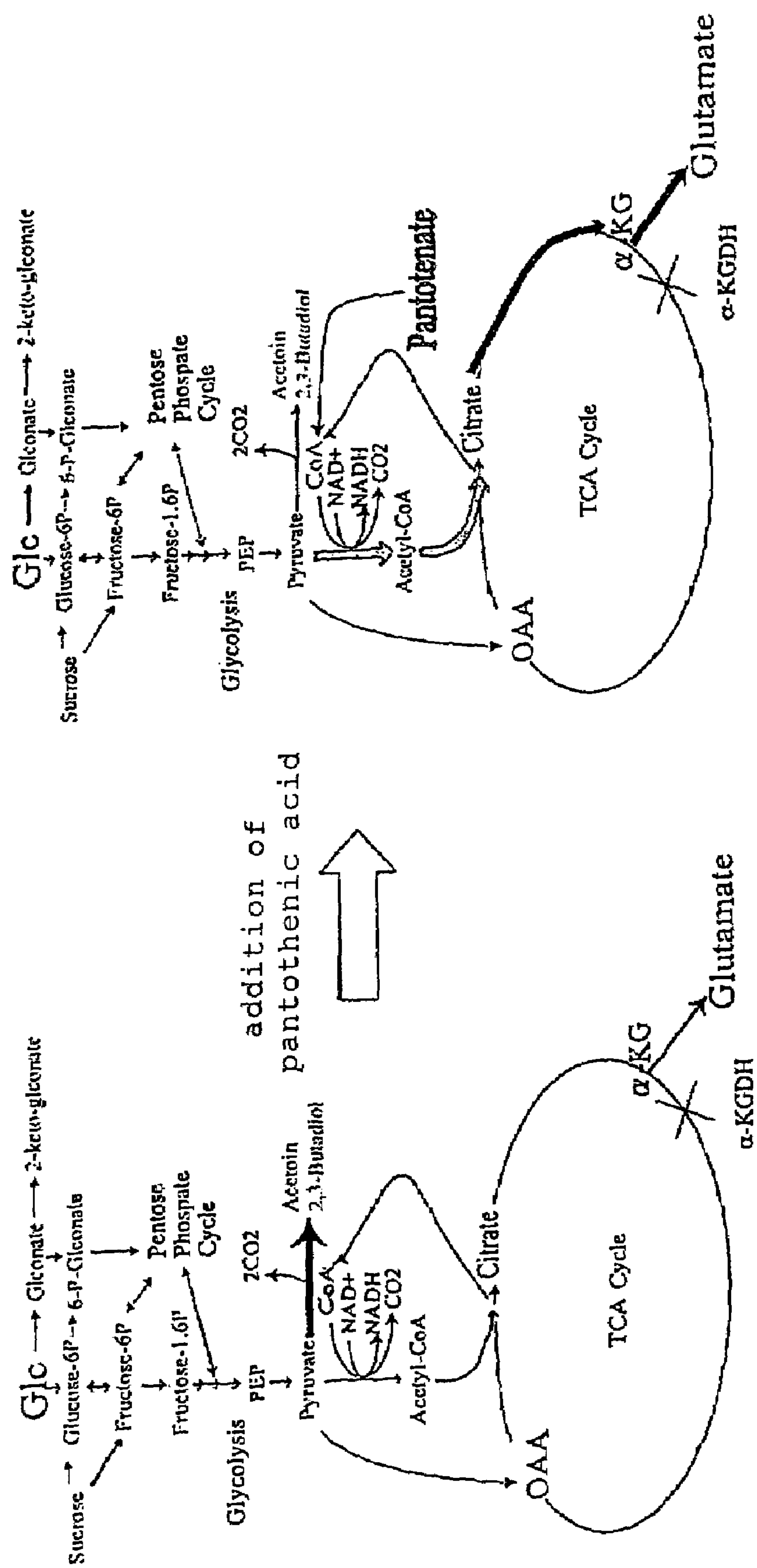
FIG. 6 is an explanatory chart showing the principle of improvement of L-glutamic acid yield provided by addition of pantothenic acid.

On the other hand, when sufficient amounts of CoA was supplied by the addition of pantothenic acid, the reaction caused by the pyruvate dehydrogenase complex (pyruvic acid->acetyl-CoA) was promoted, which reaction had served as a rate-limiting factor due to the insufficiency of CoA, and thus inflow of carbon into the TCA cycle was promoted. Thus, it is considered that the production of L-glutamic acid was promoted via α-ketoglutaric acid (αKG) as a result. Furthermore, when the production of acetoin and 2,3-butanediol decreases, $CO_2$ generated in association with the production of these substances from pyruvic acid also decreases (2 moles of $CO_2$ for 1 mole each of acetoin and 2,3-butanediol). Therefore, it is considered that this reduction also contributed to the improvement of the L-glutamic acid yield (FIG. 6).

On the basis of the above mechanism, it is considered that addition of a substance such as D-panto acid, β-alanine, or D-pantetheine instead of or in addition to the addition of pantothenic acid should provide comparable or more favorable improvement in the yield.

Example 2

Figure 7:
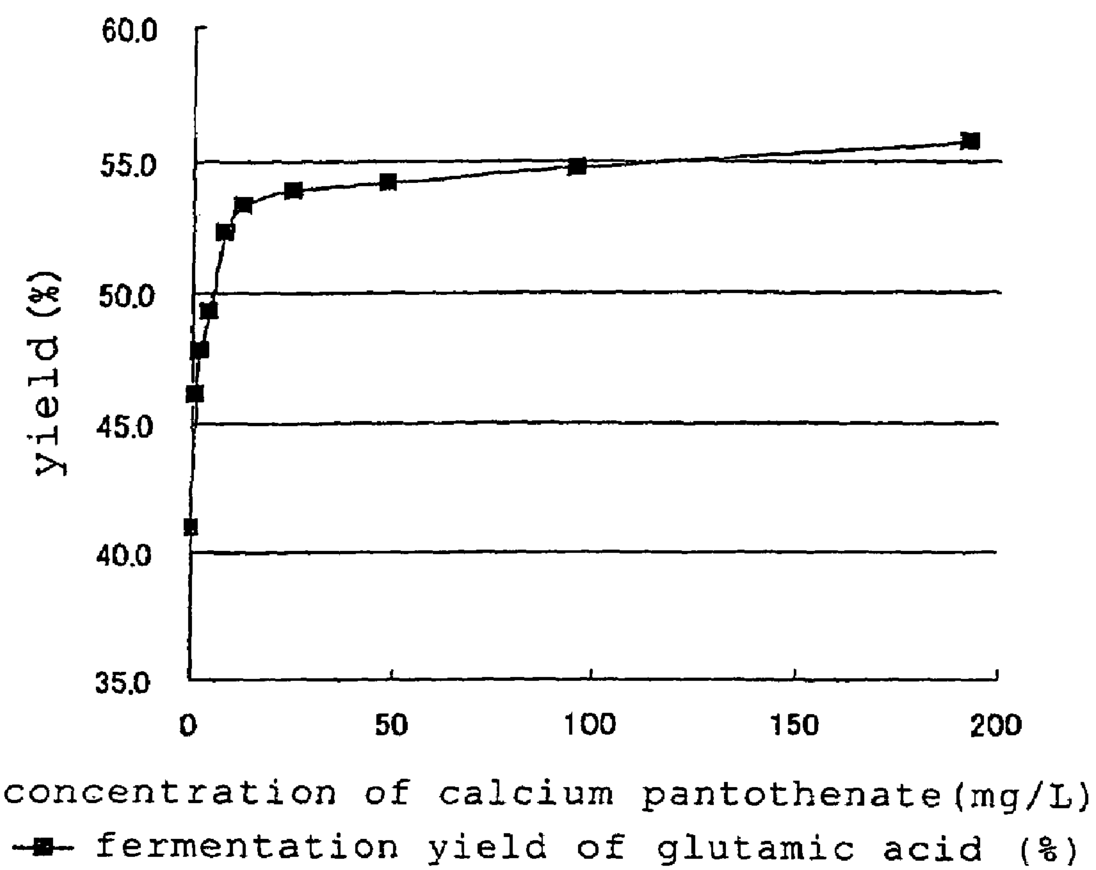
FIG. 7 is a graph showing a relationship between concentrations of calcium pantothenate added to a medium and fermentation yield of L-glutamic acid.

The concentration of calcium pantothenate to be added to the medium was changed to 0 mg/L to 196 mg/L to examine the effect of calcium pantothenate concentration on the L-glutamic acid fermentation yield. The culture was performed in the same manner as in Example 1 except that the calcium pantothenate concentration was changed to 0, 1, 2, 4, 8, 12, 24, 48, 96, or 192 mg/L. The results are shown in FIG. 7. As confirmed from these results, the L-glutamic acid fermentation yield was positively improved depending on the calcium pantothenate concentration. Even when 1 mg/L of calcium pantothenate was added, the yield was improved by about 5% compared with no addition (0 mg/L). Because the yield improvement effect could be obtained depending on the addition concentration until the added calcium pantothenate concentration reached 12 mg/L, it is considered that the yield improvement effect can be obtained even with a concentration lower than 1 mg/L.

Example 3

The main culture was performed with addition of sodium pantothenate instead of calcium pantothenate. The culture conditions were the same as those used in Example 1. Sodium pantothenate was added at a concentration of 12.15 mg/L so that the molar concentration of pantothenic acid is equivalent to that obtained with the addition of 12 mg/L of calcium pantothenate. The results are shown in Table 3.

As shown by the results, equivalent L-glutamic acid fermentation yields were obtained with calcium pantothenate and sodium pantothenate. Thus, it was clarified that the factor of the yield improvement should be pantothenic acid itself, not the counter ion of pantothenic acid.

TABLE 3

| | Addition of calcium pantothenate (12 mg/L) | Addition of sodium pantothenate (12.15 mg/L) |
|---|---|---|
| L-Glutamic acid fermentation yield (%) | 52.8 | 52.5 |

INDUSTRIAL APPLICABILITY

According to the present invention, L-glutamic acid can be more efficiently produced compared with conventional techniques by using a bacterium such as a bacterium belonging to the genus *Pantoea.*

While the invention has been described with reference to preferred embodiments thereof, it will be apparent to one skilled in the art that various changes can be made, and equivalents employed, without departing from the scope of the invention. Each of the aforementioned documents is incorporated by reference herein in its entirety. Additionally, the sequence listing material on the accompanying compact disk is hereby incorporate by reference (File Name: US-256 Seq List, Size: 83 KB, Created: Dec. 9, 2005).

The invention claimed is:

1. A method for producing L-glutamic acid comprising:

a) culturing a microorganism belonging to the genus *Pantoea* in a medium which contains pantothenic acid, wherein the pH of the medium is controlled so to induce precipitation of L-glutamic acid, and b) collecting said L-glutamic acid from said medium.

2. The method according to claim 1, wherein said microorganism is able to metabolize a carbon source in a second medium which contains L-glutamic acid at a saturation concentration and has an ability to cause accumulation of L-glutamic acid in a said second medium, wherein said second medium is at a second pH.

3. The method according to claim 1, wherein the microorganism is *Pantoea ananatis*.

4. The method according to claim 1, wherein said pantothenic acid is a pantothenic acid salt, and the concentration of said salt is at least 1 mg/L.

* * * * *